(12) United States Patent
Sarna et al.

(10) Patent No.: US 11,147,705 B2
(45) Date of Patent: Oct. 19, 2021

(54) DIASTASIS RECTI SPLINTING GARMENT

(71) Applicant: Shealena Ltd., Winnipeg (CA)

(72) Inventors: Donna Margaret Sarna, Winnipeg (CA); Jaime Erica Angus, Winnipeg (CA)

(73) Assignee: Shealena Ltd, Winnipeg (CA)

( * ) Notice: Subject to any disclaimer, the term of this patent is extended or adjusted under 35 U.S.C. 154(b) by 12 days.

(21) Appl. No.: 16/620,793

(22) PCT Filed: May 14, 2019

(86) PCT No.: PCT/CA2019/050647
§ 371 (c)(1),
(2) Date: Dec. 9, 2019

(87) PCT Pub. No.: WO2019/218059
PCT Pub. Date: Nov. 21, 2019

(65) Prior Publication Data
US 2021/0052411 A1     Feb. 25, 2021

Related U.S. Application Data

(60) Provisional application No. 62/671,559, filed on May 15, 2018.

(51) Int. Cl.
*A61F 5/03* (2006.01)
*A61C 1/08* (2006.01)
(Continued)

(52) U.S. Cl.
CPC .................. *A61F 5/03* (2013.01); *A41C 1/08* (2013.01); *A41C 1/10* (2013.01); *A61F 5/28* (2013.01); *A61F 2013/00493* (2013.01)

(58) Field of Classification Search
CPC .... A61F 5/02; A61F 5/028; A61F 5/03; A61F 2013/00493; A41C 1/08; A41C 1/10
(Continued)

(56) References Cited

U.S. PATENT DOCUMENTS

| 5,267,948 A | 12/1993 | Elliot |
| 5,613,893 A * | 3/1997 | Zagame ................... A41C 1/10 2/311 |

(Continued)

FOREIGN PATENT DOCUMENTS

| CN | 109419052 | 3/2019 |
| FR | 3072871 | 5/2019 |

*Primary Examiner* — Keri J Nelson
(74) *Attorney, Agent, or Firm* — Michael R. Williams; Ryan W. Dupuis; Ade & Company Inc.

(57) ABSTRACT

A Diastasis Recti Splinting Garment is described which includes a plurality of attached torso straps and pelvic straps which the user wraps around their body and connects to the garment so as to approximate the 2 sides of the abdominal wall, providing support to the linea alba and fascial sheathes to allow for tissue healing. Furthermore, the adjustable angled straps encircle the torso and pelvis of the user to restore the integrity of the core, providing stability to the ribcage, spine and pelvis. Restoring the integrity of the core lends itself to optimal activation of the deep core stabilizers, including the abdominal muscles as well as the musculature of the pelvic floor, back, and diaphragm. This in turn aids in dynamic stability of the spine, ribcage and pelvis. This allows maximum support of the diastasis recti, consequently facilitating tissue healing through balancing intra-abdominal pressure, while still supplying support to the vulnerable pelvic floor and stability to the spine, ribcage and sacroiliac joints.

20 Claims, 18 Drawing Sheets

(51) Int. Cl.
*A41C 1/10* (2006.01)
*A41C 1/08* (2006.01)
*A61F 5/28* (2006.01)
*A61F 13/00* (2006.01)

(58) Field of Classification Search
USPC .............. 128/96.1, 869, 870, 873, 874, 876; 602/19; 450/94, 122, 125–128, 155
See application file for complete search history.

(56) References Cited

U.S. PATENT DOCUMENTS

| | | | | |
|---|---|---|---|---|
| 6,146,240 | A * | 11/2000 | Morris | A41C 1/08 2/44 |
| 7,425,171 | B2 * | 9/2008 | Maupin | A61F 5/028 450/155 |
| 9,398,972 | B2 * | 7/2016 | Yip | A61F 5/02 |
| 9,398,973 | B1 | 7/2016 | Goodson | |
| 2009/0138064 | A1 * | 5/2009 | Horn | A61F 5/026 607/108 |
| 2015/0245939 | A1 | 9/2015 | Fruscione-Loizides | |

* cited by examiner

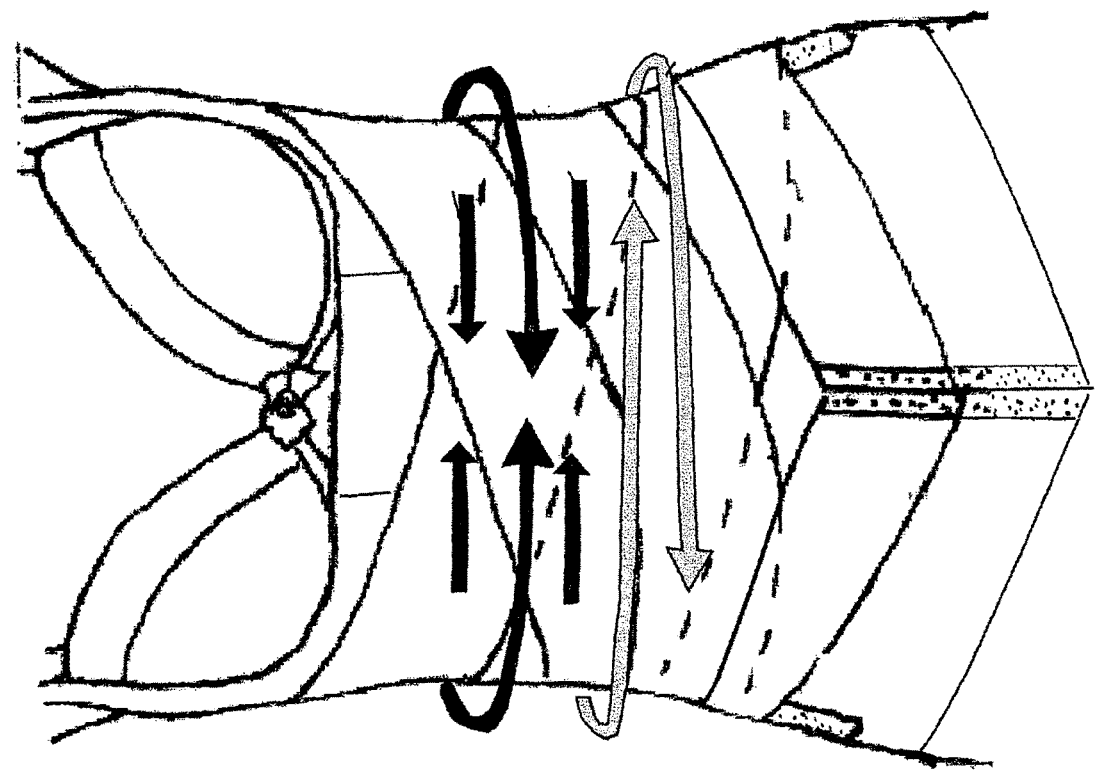
FIGURE 16-A

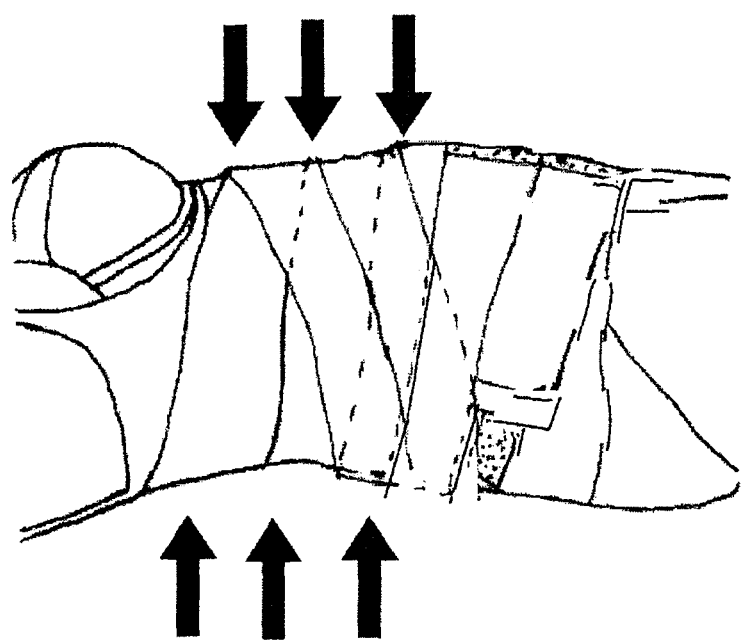
FIGURE 16-B

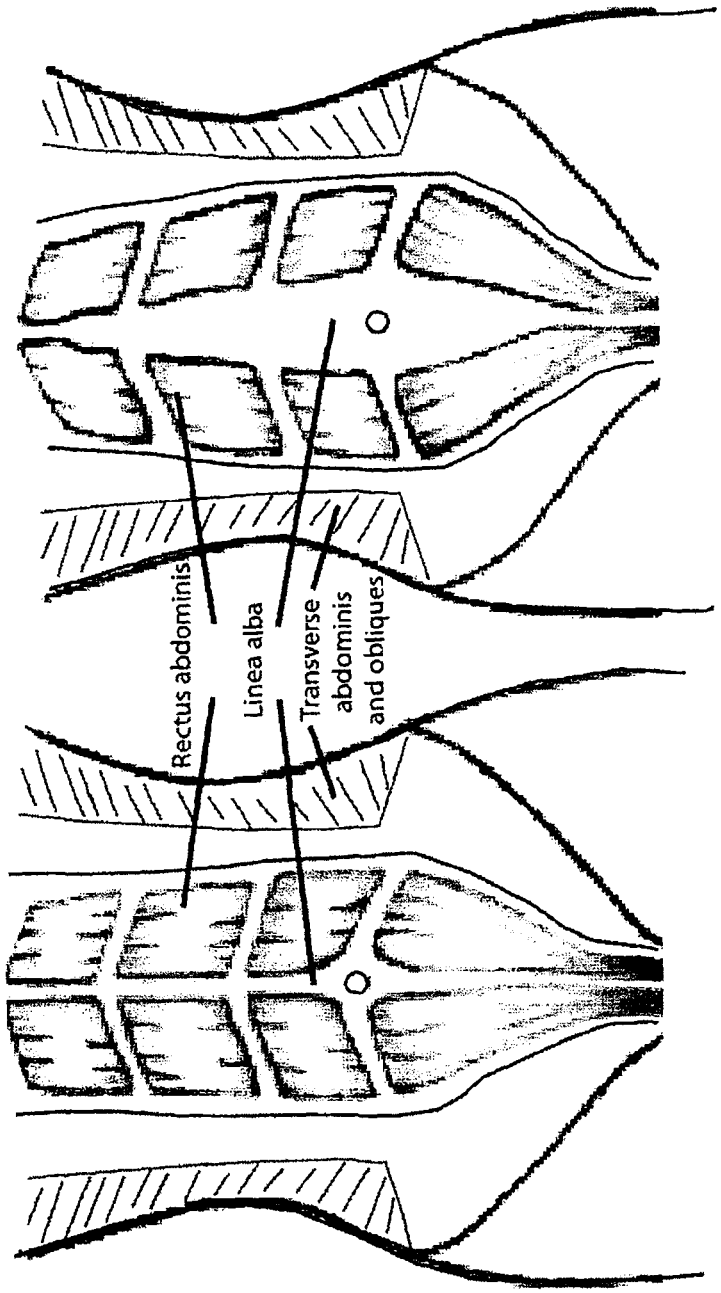

DIASTASIS RECTI SPLINTING GARMENT

PRIOR APPLICATION INFORMATION

The instant application is a 371 of PCT Patent Application CA2019050647, filed May 14, 2019, which claimed the benefit of U.S. Provisional Patent Application 62/671,559, filed May 15, 2018, and entitled "Diastasis Recti Support Body Garment", the entire contents of which are incorporated herein by reference for all purposes.

BACKGROUND OF THE INVENTION

Diastasis recti is also known as an abdominal separation and is defined as a gap of roughly 2.7 cm or greater between the two sides of the rectus abdominis muscle. The muscle separates at the midline as a result of widening and thinning of the midline tissue, known as the linea alba. The linea alba is a strong connective tissue that runs down the midline of the abdomen extending from the xiphoid process to the pubic symphysis. All of the abdominals including the transversus abdominis, internal and external obliques, as well as rectus abdominis connect into this midline connective tissue structure, either directly or indirectly through their respective fascial sheathes.

Diastasis recti in pregnant and postpartum women is caused by a combination of things, including the stretching of the rectus abdominis muscles by the growing fetus and the release of hormones during pregnancy which soften the connective tissue to prepare for birth. The increase in load results in a shift in the center of mass, altering the body's alignment and creating a subsequent increase in intra-abdominal pressure, which places a force on the abdominal wall, stretching the linea alba and fascial sheathes, causing the abdominal wall separation (FIGS. 17A and 17B).

In general, pregnant women are more susceptible to develop diastasis recti if they:
1. are over the age of 35;
2. have a high birth weight child;
3. are carrying twins; and/or
4. have had multiple pregnancies.

Additional causes can be attributed to excessive abdominal strengthening exercises after the first trimester of pregnancy. One hundred percent of women have some degree of diastasis (separation) of the rectus abdominis in the third trimester (Gilleard & Brown, 1996). For many women, the gap remains widened at 8 weeks postpartum, and if left untreated, this separation remains unchanged at 1 year postpartum (Coldron, Stokes, & Cook, 2007) (Liaw, Hsu, Liao, Liu, & HSU, 2011).

Diastasis recti presents as a ridge or a dip in the midline of the abdomen that can extend from the breast bone to below the belly button. A gap of more than 2.5 finger widths when the abdominal muscles are contracted is considered significant.

The presence of diastasis recti affects the integrity of the abdominal wall, subsequently reducing the functional strength of the torso (the abdominal wall, trunk and back). This can lead to lower back pain, pelvic instability, altered intra-abdominal pressure gradients and problems with the pelvic floor (prolapse/incontinence/pain). It is estimated that 66% of women with diastasis recti also have an issue with pelvic floor support as well as dysfunction (organ prolapse and/or stress urinary incontinence) (Spitznagle, Leong, & Van Dillen, 2007). A severe midline separation in the muscles can also lead to herniation of the intestines and other organs of the abdominal cavity and, depending upon the position of the separation, reduced stability of the ribcage.

To understand how this condition affects the body, it is necessary to understand how the core works. The inner core musculature, which provides stability for the core, is composed of 4 different muscle groups including the diaphragm, pelvic floor, transverse abdominis (deepest abdominal layer), and the multifidus (deep back muscles). All 4 of these muscles must work together to balance intra-abdominal pressure and stabilize the spine. The outer core, comprised of the primary movers such as the internal and external obliques, as well as the rectus abdominis and the erecter spinae (back extensor musculature), must work in conjunction with the inner core for optimal function. Each has a role to play. The layers of fasciae (connective tissue) that the muscles insert into (e.g., rectus fascial sheathe, thoracolumbar fascial sheathe) also play a large role in the function of the core. With muscle activation, tension is created in the fascial system, facilitating stability of the core. Thus, any defect in the fasciae/connective tissue such as what occurs at the linea alba with the abdominal separation will affect the function of the core as the muscles no longer have a stable base to attach to, nor with muscle activation will the fasciae/connective tissue be able to provide tensile force to aid in stability of the spine, pelvis and ribcage, nor indirectly aid in balancing intra-abdominal pressure. Stability is necessary for daily function. Balanced intra-abdominal pressure is necessary for continence, optimal function of the diaphragm as well as in preventing prolapse and pelvic floor dysfunction.

The connection of the muscles to their boney and fascial attachments is necessary for optimal function of the core. In a normal situation with an intact midline linea alba, there is no midline abdominal separation. The abdominal muscles wrap around the torso, attaching to the ribcage and pelvis and in front to their respective fascial sheathes, which in turn connect into the linea alba. The muscles wrapping around the torso also connect in the back attaching to the layered thoracolumbar fascial sheathe. The thoracolumbar sheathe also surrounds key muscles in the back creating a closed cylinder. This along with the pelvic floor and diaphragm creates an integrated connected system (canister) necessary for optimal function of the core. It is imperative for function that this integrated system is intact.

The thinning and stretching of the linea alba and the associated fascial sheathes associated with a diastasis recti creates separation of the abdominal muscles at midline, which in turn has a significant effect on physical and functional ability.

The separation does not allow for a stable base of attachment for the muscles, which in turn does not allow for optimal activation or function of the muscles. Consequently, abdominal compression and organ support is impaired, as is stability of the core, ribcage, pelvis and spine as well as control of intra-abdominal pressure. Physical activity and daily function, especially in certain positions, may be compromised and potentially lead to a worsening of the abdominal separation.

Diastasis Recti can be helped with splinting. Specifically, the splint draws the two sides of the abdominal muscles together, approximating the gap and stabilizing the system to allow the connective tissue to heal. Optimal tissue healing improves the integrity and the function of the canister long term. Splinting also provides support and stability for weakened muscles to prevent secondary injuries to the back, sacroiliac joints, and pelvic floor (prolapse).

It also provides sensory awareness to help maintain the activation of the core muscles with everyday activity.

Splinting is recommended with a separation in the early postpartum period (first 8 weeks) but may be necessary beyond this, depending on the extent of the separation. Splinting is used to assist the body to heal in optimal position and reduce injury, but it is not to be used in isolation. Addressing deficits and restrictions in alignment is of key importance in recovery, as is the implementation of a global strengthening program.

SUMMARY OF THE INVENTION

According to one aspect of the invention, there is provided a Diastasis Recti splinting garment comprising:
- a body suit comprising:
  - a front panel arranged to apply compression to the abdominal wall of a user;
  - a back panel having an upper portion, and a lower portion, the lower portion having a rear connection panel; and
  - at least two torso straps, said at least two torso straps arranged to be pulled and wrapped around the torso of the user in a downward oblique angle and connect to the rear connection panel on the lower portion of the back panel; and
  - an attachable pelvic strap arranged to be pulled and wrapped around the pelvis of the user at an upward oblique angle.

As can be seen with reference to the drawings, there is at least one torso strap on each side of the body suit.

In some embodiments, the back panel has a three layered upper portion, with two layers comprising or consisting of compression fabric and a third center or middle layer comprising or consisting of two horizontal elastic straps.

In other embodiments, the back panel may have a three layered upper portion: two layers composed of compression fabric and a third center layer comprising at least two diagonal elastic straps.

In some embodiments, the lower portion is a two layered lower portion, the lower portion further comprising or having a rear connection panel.

In some embodiments, there are at least two torso straps, said at least two torso straps being arranged to be or capable of being pulled and wrapped around the torso of the user and attached to the rear connection panel on the lower portion of the back panel and in some embodiments on the inner pelvic strap as discussed herein.

In some embodiments, each torso strap is arranged to wrap around the torso of the user in an oblique downward crossover starting on a first side of the midline of the user so that each respective adjustable torso strap crosses the midline of the user and connects to the rear connection panel on a second side of the midline of the user. The torso straps are attached simultaneously or sequentially.

In some embodiments the 2 right and 2 left torso straps may be connected specifically at the VELCRO® (hook and loop fastener) attachment point at the end of the straps. In these embodiments, there is no connection between the straps other than at this point allowing for adjustability by the user.

In some embodiments, the garment includes adjustable shoulder straps.

In some embodiments, the garment includes a groin panel which is arranged to be opened or is capable of being opened by the user without removal of the garment.

In some embodiments, the pelvic strap is a dual strap comprising an attachable inner pelvic strap with both right and left arms thereof arranged to be pulled and wrapped around the pelvis of the user in an upward oblique angle specific to the user's needs and a bladder support strap arranged to be wrapped around the user in an upward oblique angle. In some embodiments, the inner aspect of the inner pelvic strap, in contact with the bodysuit, has 3 rows of silicon gripper gel.

As discussed herein, the inner pelvic strap can be used as a base strap for connection with other straps. For example, the bladder support strap is arranged to be or capable of being attached to the inner pelvic strap.

In some embodiments, there is provided an attachable abdominal strap that is arranged to be or capable of being or for being wrapped around the abdomen of the user for providing additional abdominal support, as discussed herein. The strap acts in conjunction with the bladder support strap to provide compression to the abdominal wall as well as balance the downward intra-abdominal gradient created from the torso straps above. For example, right and left arms thereof are capable of being or arranged to be pulled and wrapped around the user in an upward oblique angle. In some embodiments, the inner aspect of the strap, in contact with the bodysuit, has 3 rows of silicon gripper gel.

In some embodiments, there is provided an attachable wide torso strap that is arranged to be wrapped around the torso of the user so as to provide additional support for the torso of the user, as discussed herein. Specifically, this strap provides a compressive force to the user's torso rather than just the abdomen, as discussed herein.

In some embodiments, there are four torso straps, arranged such that a respective two adjustable torso straps are attached to each side of the body suit.

In some embodiments, the garment includes adjustable shoulder straps.

According to another aspect of the invention, there is provided a method of supporting the abdomen, ribcage, low back, sacroiliac joints and pelvic floor of an individual suffering from diastasis recti, said individual having a body, a torso, a lower back, a ribcage, sacroiliac joints, an abdomen, a midline, abdominal musculature, a pelvis and a pelvic floor, said method comprising:
  providing a Diastasis Recti splinting garment comprising:
    a body suit comprising:
      a front panel arranged to apply compression to the abdominal wall of the individual;
      a back panel having an upper portion, and a lower portion, the lower portion having a rear connection panel; and
      at least two torso straps, said at least two torso straps arranged to be pulled and wrapped around the torso of the user and connect to the rear connection panel on the lower portion of the back panel; and
    a pelvic strap that is arranged to be pulled and wrapped around the pelvis of the user on an upward oblique angle;
  the user:
    (i) entering the body suit and positioning the body suit on the body of the user such that the front panel of the garment is placed on the abdominal wall of the user, thereby providing compression to the abdominal wall of the user;
    (ii) grasping one of the at least two torso straps at a free end thereof and pulling and wrapping said one of the at least two torso straps around the torso of the user on a downward oblique angle, crossing the free end over the midline of the individual and continuing the wrap around the torso and pelvis to attach the free end to the rear connection panel on the opposite side.

(iii) repeating step (ii) for each torso strap; wherein the action of ii and iii thereby stabilizes the ribcage, trunk, abdomen and back of the user, approximating the right and left sides of the abdominal musculature.

(iv) grasping a first end of the pelvic strap and pulling and wrapping the first end of the pelvic strap around the pelvis of the user on an upward oblique angle and connecting the first end to the rear attachment panel, thereby providing compression across the respective sacroiliac joint of the user and supporting the lower back and the abdomen of the user; and (v) grasping a second end of the pelvic strap and pulling and wrapping the second end of the inner pelvic strap around the pelvis of the individual at an upward oblique angle and connecting the second end to the rear attachment panel, thereby providing compression across the sacroiliac joints of the individual and supporting the lower back and the abdomen of the individual.

In some embodiments, the pelvic strap comprises an inner pelvic strap and a bladder support strap, arranged to be wrapped around the user on an upward oblique angle.

In these embodiments, the method further comprises step (vi), grasping the first and second arms of the bladder support strap, which attach at a center front of the inner pelvic strap, and pulling both arms upward on an oblique angle and connecting them to the inner pelvic strap, thereby providing support for the bladder, pelvic floor and abdomen of the user as well as balancing the intra-abdominal pressure gradient from below.

In some embodiments, there is provided an attachable abdominal strap. In these embodiments, the method includes an additional step after the pelvic strap has been engaged, comprising grasping first and second arms of the abdominal strap and pulling both arms on an upward oblique angle, thereby providing support to the abdominal wall and balancing the intra-abdominal pressure gradient from below. In these embodiments, based upon the user's needs the straps may attach to the rear connection panel, or to ends of torso straps or ends of inner pelvic straps individually or in an overlapping manner with said straps. Based upon the user's needs, the point of origin of the abdominal strap can be directly and solely on the front attachment of the inner pelvic strap above the bladder support strap or it can be placed in an overlapping manner with the bladder support strap with a shared point of origin from the front attachment of both of the straps (inner pelvic and bladder support).

In some embodiments, there is provided an attachable wide torso strap. In these embodiments, the method comprises an addition step comprising of grasping one end of the non-attached wide torso strap, connecting it to the back panel or the inner pelvic strap or back of the torso straps depending upon individual needs and wrapping the strap around the torso in an oblique manner connecting the free end onto the body of the strap. Utilization of this strap is determined by the user's needs.

BRIEF DESCRIPTION OF THE DRAWINGS

FIG. 16 A and FIG. 16 B—is a front and side view of the Diastasis Recti Splinting Garment. Small arrows demonstrate approximation and compression of the abdominal wall, created by the right and left set of torso straps as they wrap around the torso across the midline to attach on the opposite side of the lower rear panel. The larger arrows encircling the torso and ribcage, represent the role of the adjustable set of torso straps in closing the upper and middle portions of the cylinder providing a compression force to stabilize the abdomen, ribcage, trunk and back for core activation and abdominal support and approximation. It also facilitates the balance of intra-abdominal.

FIG. 17A shows a normal abdomen schematically.

FIG. 17 B shows a Diastasis Recti abdomen schematically.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Described herein is a Diastasis Recti Splinting Garment 1 designed to mimic the anatomy and function of the core. As discussed herein, the garment is arranged to be adjustable to balance the intra-abdominal pressure, aid in spinal, ribcage and sacroiliac stability as well as provide support to the pelvic floor and associated organs. These are all issues that may be experienced by postpartum women presenting with a diastasis recti. Its design allows for flexibility of adjustment so that it can be specifically fitted to and adjusted by each individual user. This allows maximum support of the diastasis recti, consequently facilitating tissue healing through balancing intra-abdominal pressure, while still supplying support to the vulnerable pelvic floor and stability to the spine, ribcage and sacroiliac joints.

Furthermore, the Diastasis Recti Splinting Garment 1 is designed to restore the integrity and function to the core, facilitating a return to normal activity. It is an integrated garment with its components having various roles which mimic the anatomy and which together create a unique, adjustable splinting garment addressing the needs of postpartum moms. The garment has been designed to achieve the following:

1. Approximate the two sides of the abdominal wall to facilitate core integrity;
2. Restore abdomen integrity for organ support;
3. Restore the function of the core musculature facilitating optimal activation;
4. Restore the stability of the core;
5. Balance intra-abdominal pressure;
6. Provide pelvic floor and organ support; and/or
7. Restore ribcage, spinal and pelvic stability.

Figure 1:
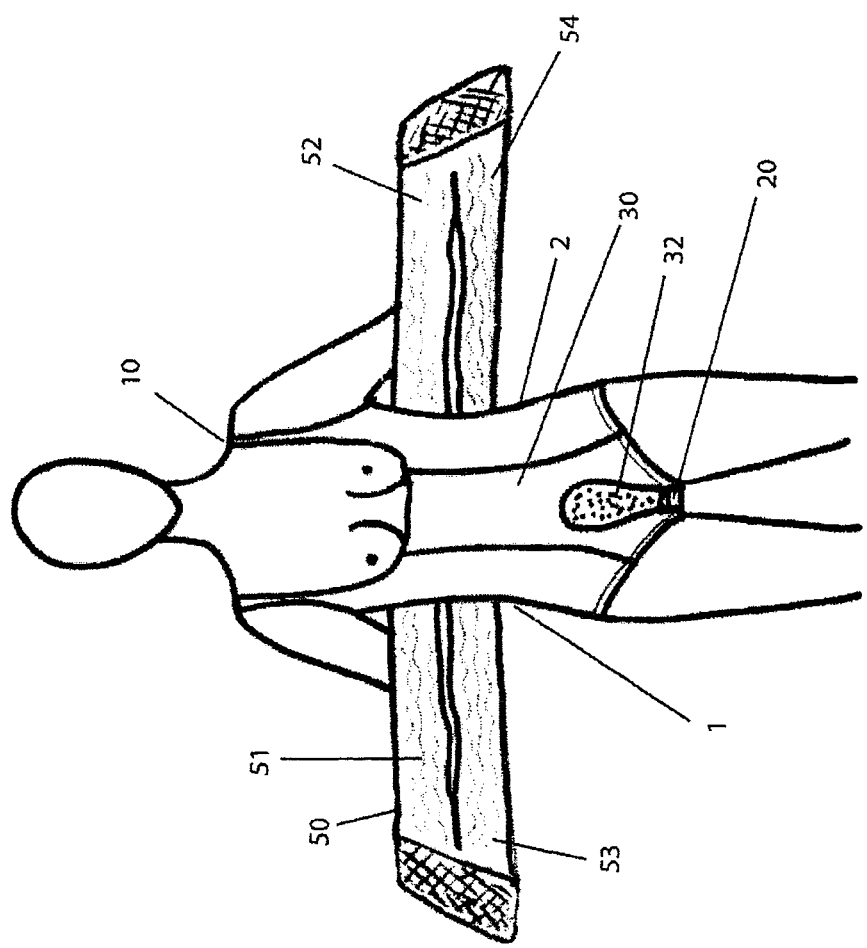
FIG. 1—is a front view of the Diastasis Recti Splinting Garment in use.
Figure 2:
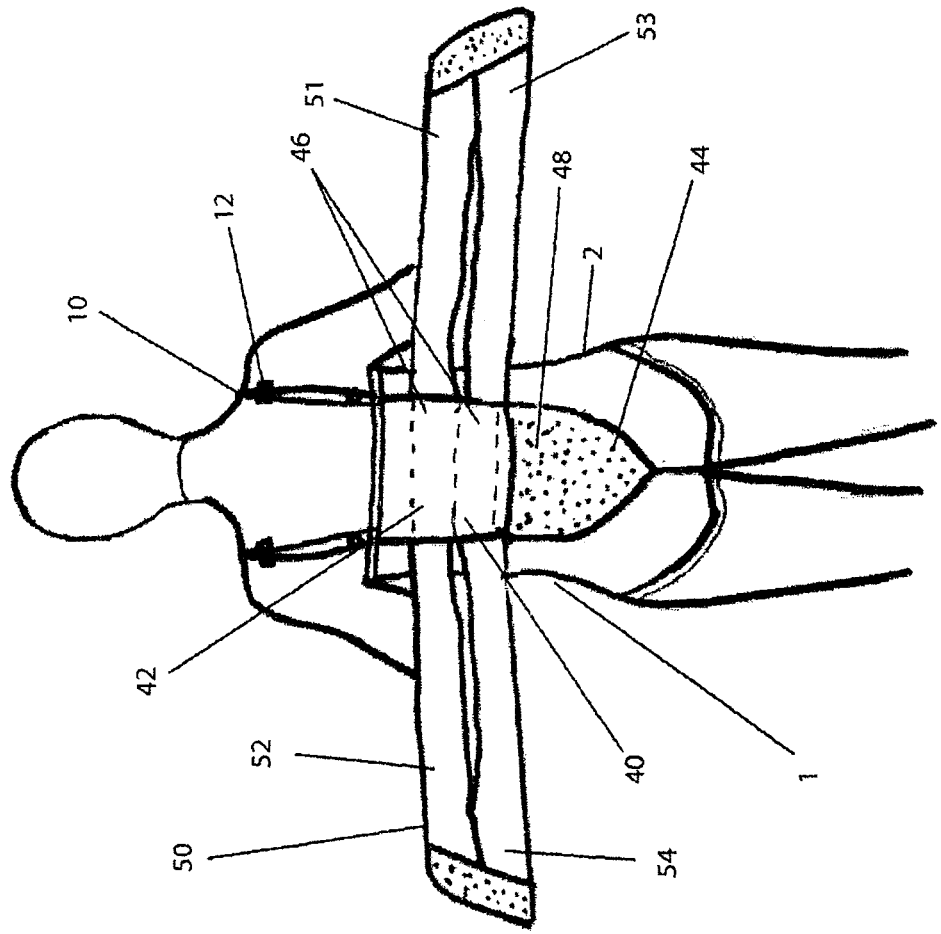
FIG. 2—is a rear view of the Diastasis Recti Splinting Garment in use.
Figure 3:
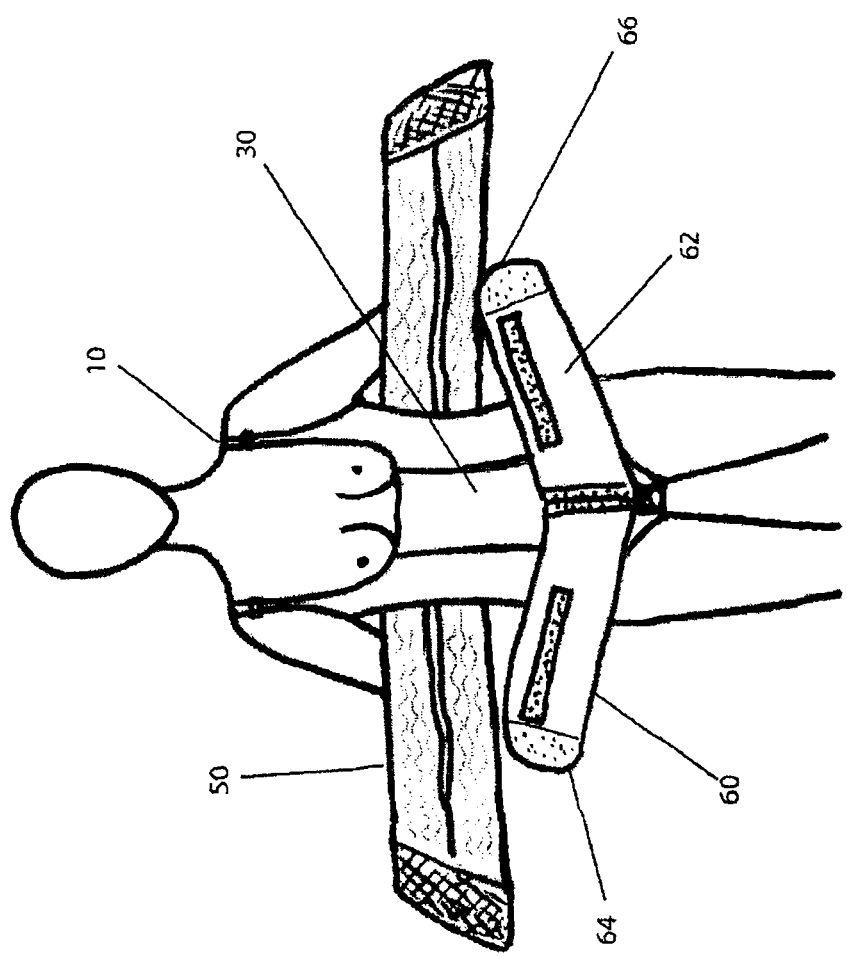
FIG. 3 is a front view of the Diastasis Recti Splinting Garment showing the pelvic straps engaged.

As discussed herein and as shown in FIGS. 1-3, the Diastasis Recti Splinting Garment 1 comprises: a body suit 2; shoulder straps 10; a groin panel 20; a front central panel 30; a back central panel 40; torso straps 50; and pelvic strap 60.

As will be apparent on review of the accompanying figures, the term "body suit" does not necessarily refer to a garment that covers the entire body of the user. For example, a "body suit" does not necessarily extend to include long sleeves which cover the arms of the user or leggings to cover the legs of the user. The body suit 2 design creates a garment 1 that prevents movement and slippage of the garment 1 during activity. In some embodiments, the body suit is made of a stretch compression fabric with a moisture management anti-microbial finish.

As can be seen in FIGS. 1-3, the shoulder straps 10 scoop under the breasts, making it ideal for women to nurse comfortably without having to remove the garment. As can be seen in FIG. 2, the shoulder straps 10 include adjustment means 12 for adjusting the shoulder straps 10, as discussed below.

The groin panel 20 is arranged to be releasable for opening of the panel for ease of toileting, that is, so that the garment does not need to be removed. In some embodiments, the groin panel 20 is closed with a hook and eye arrangement, although other suitable arrangements will be readily apparent to one of skill in the art.

The front central panel 30 includes an attachment region 32 for connecting the pelvic strap 60 to the body suit 2, as discussed below. Specifically, the front central panel 30 creates a compression force as well as allows for an attachment point for the pelvic strap 60 that can be adjustable to allow for individual differences in body proportions. Thus, the front central panel 30 provides a stable base of support on which the adjustable pelvic strap arms 60 pull from, as discussed below.

In some embodiments, the front central panel 30 is fabricated out of two layers of compression material.

Figure 4:
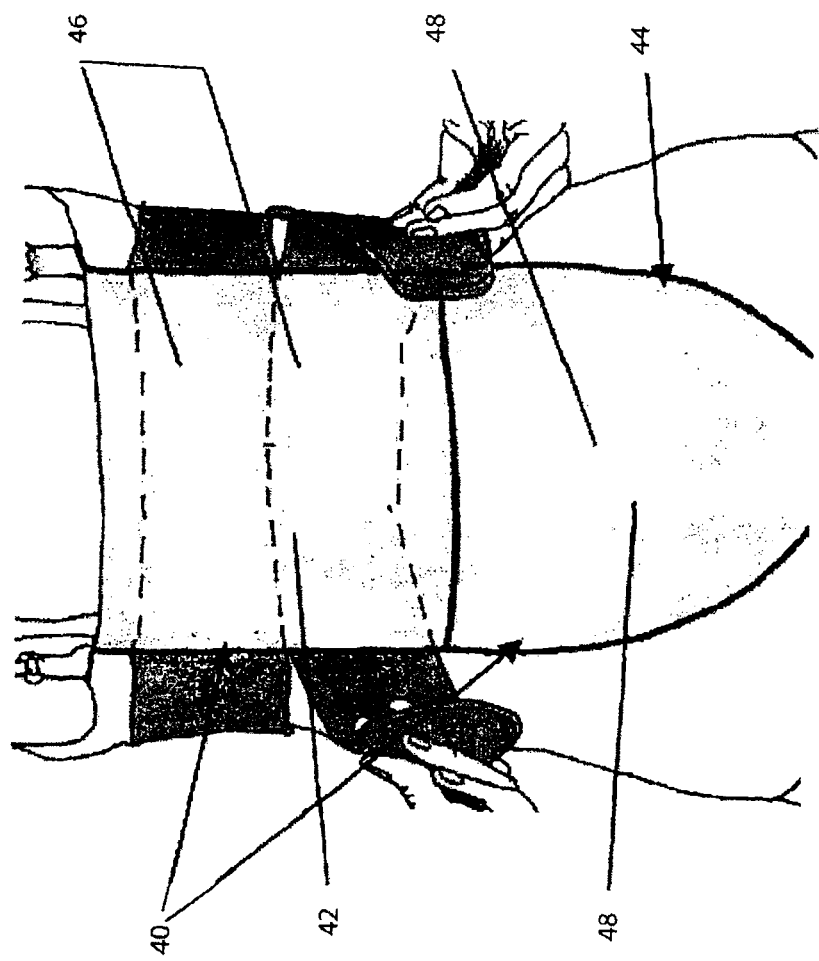
FIG. 4—is an isolated view of the rear panel.
Figure 5:
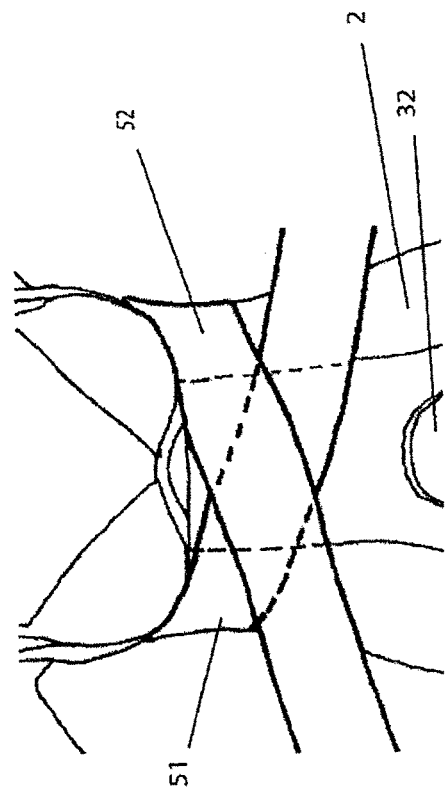
FIG. 5—is a front view of the Diastasis Recti Splinting Garment showing crossing of the upper torso straps.
Figure 6:
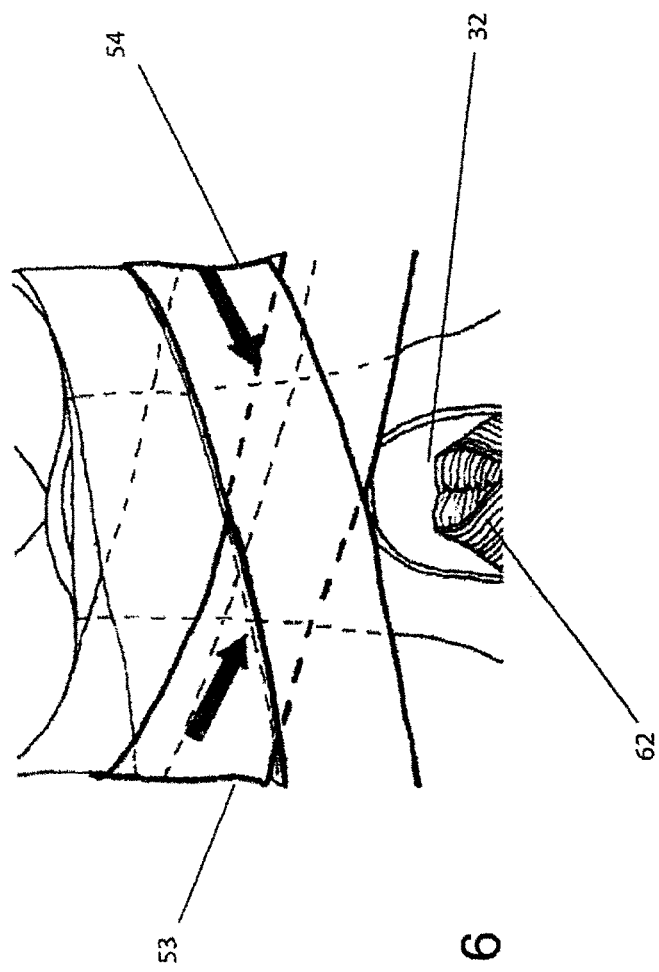
FIG. 6—is a front view of the Diastasis Recti Splinting Garment showing crossing of the lower torso straps over the upper torso straps. Arrows show direction of pull and compression.
Figure 7:
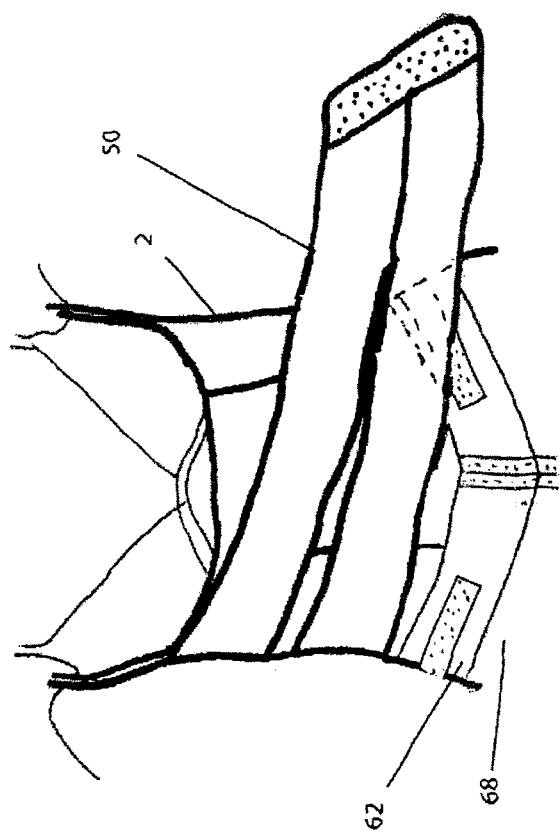
FIG. 7—is a front view of the Diastasis Recti Splinting Garment showing the crossing of the right torso straps (upper and lower) across the midline of the user's torso, overlapping the left arm of the bladder support strap as well as the inner pelvic strap.
Figure 8:
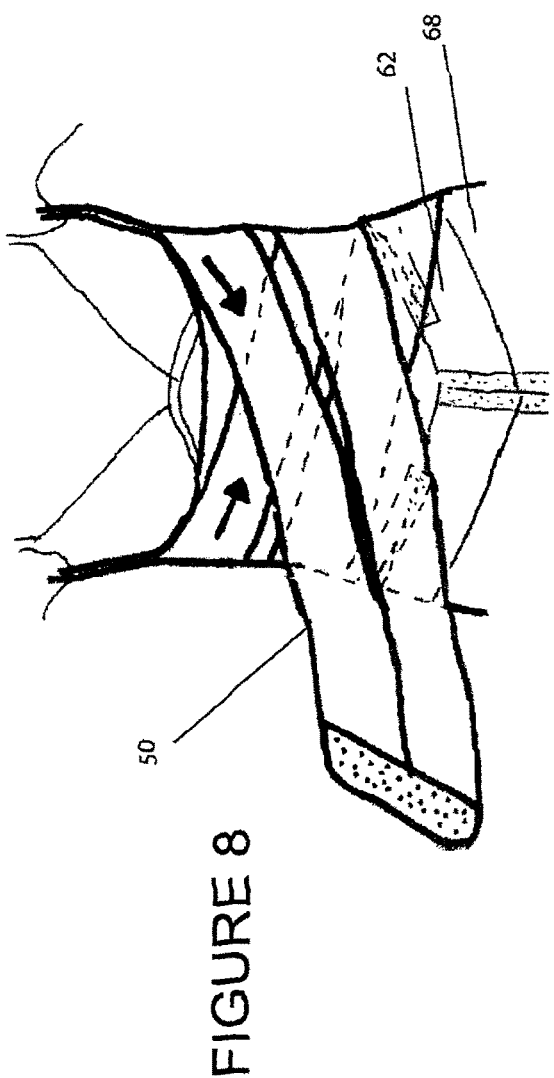
FIG. 8—is a front view of the Diastasis Recti Splinting Garment showing the crossing of the left torso straps (upper and lower) across the midline of the user's torso, overlapping the right torso straps as well as the right arm of the bladder support strap and inner pelvic strap. Arrows indicate the direction of pull and compression by the user on the arms of the strap while wrapping around the torso.

The back central panel 40 is divided into an upper portion 42 and a lower portion 44, as shown in FIG. 4. In some embodiments, both the upper portion 42 and the lower portion 44 comprise double, layers of fabric. In some embodiments, the outside layer of the upper portion 42 of the back central panel 40 is made of compression fabric.

In some embodiments, the back panel has a 3 layer upper portion and a 2 layer lower portion with the inner layer being continuous between the two portions. The 3 layers of the upper portion consisting of 2 layers of compression fabric with the middle layer consisting of 2 horizontal elastic straps. The inner layer of the lower portion of the rear connection panel may be of compression fabric and the top layer may be of loop fabric.

The upper portion 42 includes two stretchable horizontal straps 46 that are connected to the torso straps 50 as discussed herein. Each stretchable horizontal strap 46 allows for tension to be created when the torso straps are engaged, as discussed herein.

As discussed herein, there are at least two torso straps which are arranged to be pulled and wrapped around the torso of the user. The torso straps may be attached to the rear connection panel on the lower portion of the back panel and/or in some embodiments the inner pelvic strap.

In some embodiments, the inner layer of the lower portion 44 is a continuation of the compression fabric from the upper portion 42.

The outer layer of the lower portion 44 of the back central panel 40 has an attachment panel 48 for connection of the torso straps 50 and the pelvic strap 60 as discussed herein.

The torso straps 50 function to re-establish an intact cylinder by approximating the right and left sides of the abdominal musculature that separates in the presence of a diastasis recti. The torso straps 50 also create abdominal compression, which together with the approximation allows for tissue healing at the area of separation (linea alba) when the garment 1 is in use, as discussed below.

As discussed above, the torso straps 50 are connected at a first end thereof to the horizontal strap 46 of the upper portion 42 of the back central panel. In some embodiments, there are at least two torso straps, arranged such that there is one torso strap on each side of the body suit. In the embodiments shown in FIGS. 1-3, there are four torso straps: upper right torso strap 51, upper left torso strap 52, lower right torso strap 53 and lower left torso strap 54.

In some embodiments the two right and two left torso straps may be connected such that the two right straps can be moved in unison by grasping one of the straps. For example, there may be a VELCRO® (hook and loop fastener) attachment point at the end of the straps and there may be no connection between the straps other than at this point allowing for adjustability by the user, although other suitable arrangements may also be used. In some embodiments, there are 3 rows of silicon gripper gel on the inner aspect of the torso straps that are in contact with the bodysuit.

The pelvic strap 60 is arranged to be attached to the attachment region 32 on the front central panel 30. This allows each individual user to customize the exact placement of the attachment, based upon their body's dimensions for best fit, optimizing comfort and support.

In some embodiments, the pelvic strap 60 is a dual strap comprising an inner pelvic strap 62 having a right arm 64 and a left arm 66 and a bladder support strap 68 having a first arm 70 and a second arm 72.

The right arm 64 and the left arm 66 of the inner pelvic strap 62, are arranged to be wrapped around the right and left sides of the pelvis at upward oblique angles, as discussed below.

The bladder support strap 68 acts as a sling for the bladder and provides support for the generally weakened postpartum pelvic floor by providing support from below. As discussed below, in use, the first arm 70 and the second arm 72 are pulled and wrapped around the body of the user and attached to the straps 64 and 66 respectively at an upward angle relative to the attachment region 32.

In other embodiments, the pelvic strap is an attachable inner pelvic strap as described above and the garment includes a detachable bladder support strap with both the right and left arms arranged to be pulled and wrapped around the pelvis of the user in an upward oblique angle. For example, the detachable bladder support strap may include a VELCRO® (hook and loop fastener loop fabric proximal to the middle of one face of the strap and VELCRO® (hook and loop fastener) hook fabric proximal to the middle of the underside. In these embodiments, the inner aspect of the strap, in contact with the bodysuit, has 3 rows of silicon gripper gel. The arms of the detachable bladder strap may be pulled upwards on an oblique line from the center attachment point and pulled laterally around the pelvis to the right and left. The ends of each arm of the detachable bladder strap may include VELCRO® (hook and loop fastener) hook fabric for connecting the arms of the detachable bladder strap to other elements of the garment, as discussed herein.

Figure 20:
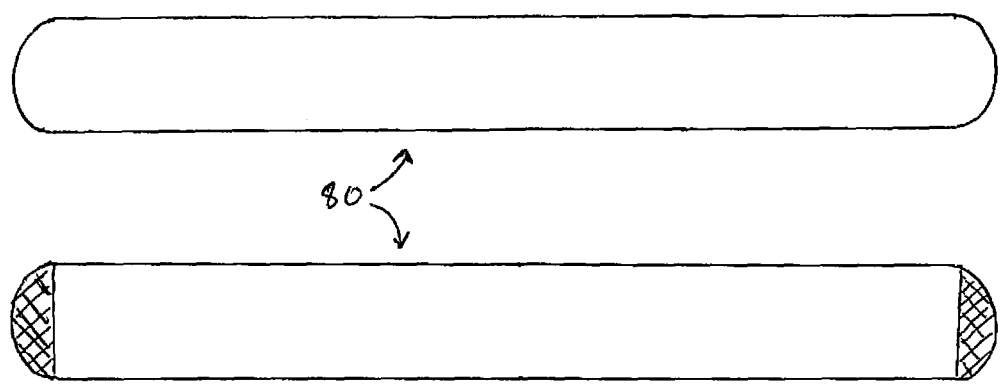
FIG. 20 is a front and rear view of the attachable wide torso strap.

As discussed above, in some embodiments, there is also provided a wide torso strap 80, shown in FIG. 20, which is wider than the adjustable torso straps 51, 52, 53, 54. As will be appreciated by one of skill in the art, exact placement and tension is determined by the individual user. In these embodiments, the attachable wide torso strap 80 is pulled and wrapped around the body of the user on a diagonal angle and is utilized to close the cylinder, supplying additional compression in the abdominal region, where required, as well as support the approximation, as discussed below.

In some embodiments, the garment includes a detachable abdominal strap 81 with both the right 82 and left 83 arms arranged to be pulled and wrapped around the user in an upward oblique angle. The inner aspect of the strap, in contact with the bodysuit, has 3 rows of silicon gripper gel. In the drawings, the ends of the detachable abdominal strap are shown as having a substantially square-like shape; however, in other embodiments, the ends may be tapered and/or curved.

For use of the garment 1, the user enters the body suit 2 such that the body suit 2 fits around their body as shown in FIGS. 1-3.

If necessary, the user may adjust the lengths of the shoulder straps 10 using the adjustment means 12 so that a more comfortable fit is achieved. As will be apparent to one of skill in the art, adjustments for fit may be minor or may not be necessary during subsequent uses.

Specifically, the body suit 2 is positioned on the body of the user such that the front central panel mimics the placement of the rectus abdominis muscle, as well as the associated fascial sheathes of the rectus and the other abdominal musculature (transversus abdominal, internal oblique, external oblique). Functionally, the front central panel mimics one of the primary functions of the abdominal muscles and their associated sheathes, that of compression.

As discussed above, the torso straps 50 are pulled and wrapped simultaneously or sequentially around the torso at a downward oblique angle such that a second end of the strap engages with and is connected to the attachment panel 48 on the lower portion 44 of the back central panel 40.

In some embodiments, depending on the sequence in which the elements of the garment are engaged by the user, the torso straps may also attach over the pelvic strap, for example, the inner pelvic strap in an overlapping manner, as discussed herein.

For example, right upper torso strap 51 and left upper torso strap 52 are grasped by the user, and pulled and wrapped around their torso crossing the user's midline. The user then connects the straps 51 and 52 to the lower portion of the back central panel 48. If there are more than two torso straps and/or if the straps on each side are not connected, this process is repeated for the right lower torso strap 53 and the left lower torso strap 54. The torso straps 51, 52, 53, 54 effectively crisscross over one another.

As discussed above, the connection of the torso straps 50 to the stretchable horizontal strap 46 on the back central panel 40, as shown in FIG. 4, allows for a greater amount of tensile force to be created by the pull. This allows the user to adjust the tension according to their needs. Furthermore, the torso straps 50 are arranged such that the user can adjust each torso strap 50 during this process so the exact oblique angle that is of greatest comfort and support to them for each torso strap 51, 52, 53, 54 can be determined.

As discussed below, the torso straps 50 wrap on the diagonal which mimics the direction of the fibers of the external oblique muscles, approximating the right and left sides of the abdominal musculature and creating a compression force as they cross midline. This can be visualized by consulting FIGS. 5-8, which show how the wrapping and engagement of the torso straps 50 provide support that mimics the action and function of the core musculature.

In some embodiments, the pelvic strap 60 is arranged to be connected to the body suit 2 at the attachment region 32 of the front central panel 30, which is situated when in use in the region below the belly button, at the level of the pubic bone of the user.

Figure 9:
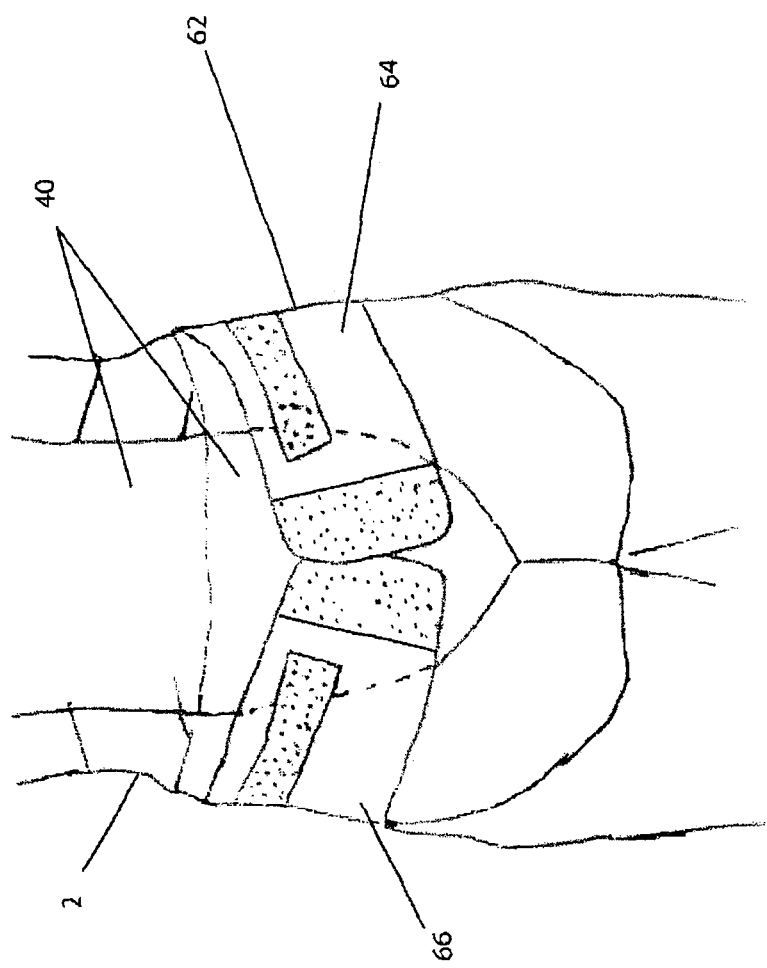
FIG. 9—is a rear view of the engagement of the inner pelvic strap around the pelvis of the user and connection to the lower back panel of the Diastasis Recti Splinting Garment.

Once the pelvic strap 60 is connected to the body suit 2, the user grasps the right arm 64 of the inner pelvic strap 62 and pulls and wraps the right arm 64 around their pelvis at a upward oblique angle and connects the right arm 64 of the inner pelvic strap 62 to the attachment panel 48 on the back central panel 40. This process is repeated on the opposite side for the left arm 66 of the inner pelvic strap 62, as shown in FIG. 9.

The inner pelvic strap 62 has multiple functions. The first is to aid in pelvic and core stability. It provides mild compression across the sacroiliac joints, as well as support to the low back and abdomen, which can be visualized by reviewing FIGS. 3 and 9. Low back pain and sacroiliac pain are primary complaints from individuals with Diastasis Recti.

Figure 13:
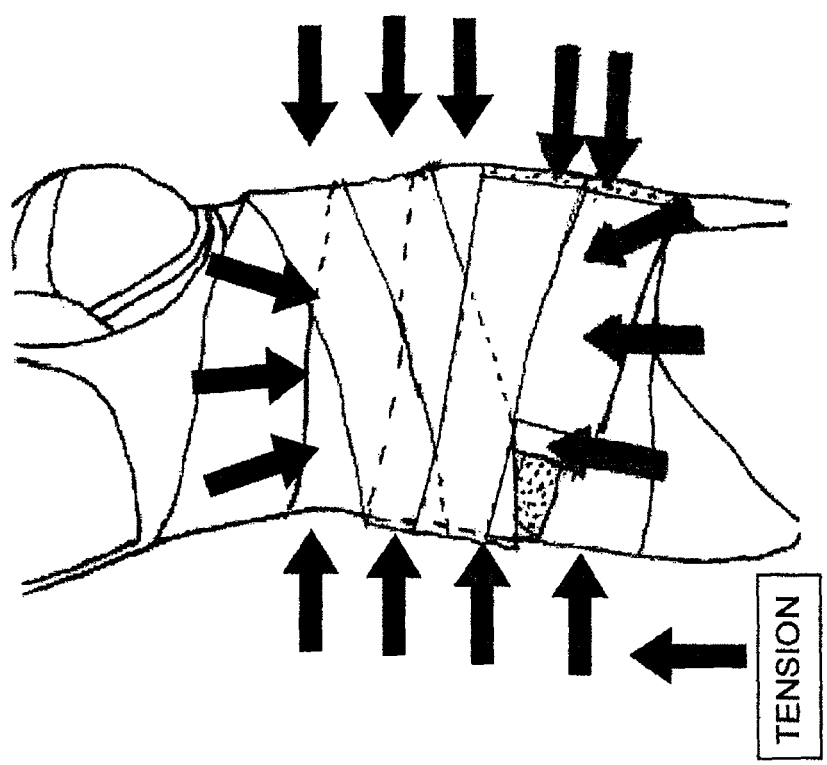
FIG. 13—is a side view of the Diastasis Recti Splinting Garment. The garment, with the front and back panels as well as the adjustable torso, abdominal, bladder support as well as inner pelvic straps allows for approximation of the abdominal wall as well as provides the user with the ability to balance intra-abdominal pressure. The user balances the intra-abdominal pressure by the amount of tension that they generate as they pull on the straps as well as by the oblique angle that they use. The arrows show the direction of compression on the body of the user as well as the intra-abdominal pressure gradients from engagement of the inner pelvic, bladder support, torso, and abdominal straps. The torso straps create compression with a downward intra-abdominal pressure gradient, which is balanced by the lower inner pelvic, bladder support and abdominal straps, which create compression with an upward intra-abdominal pressure gradient. In this way the garment mimics the body's functional ability to respond to changes in intra-abdominal pressure. It also supports abdominal wall integrity, provides organ support, optimizes core muscle activation and facilitates spinal, ribcage and pelvic stability.
Figure 14:
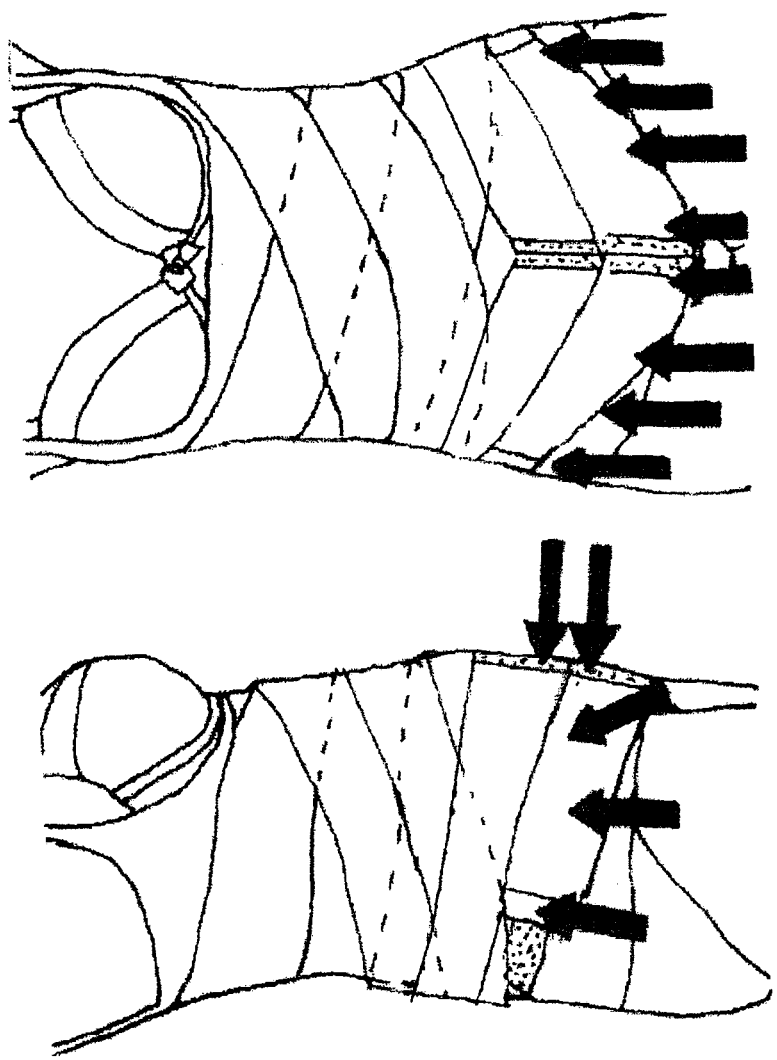
FIG. 14-A and FIG. 14-B is a front and side view of the Diastasis Recti Splinting Garment highlighting the function of the bladder support strap as well as the abdominal strap. Arrows show the direction of compression as well as the upward intra-abdominal pressure gradient created by these straps as they support the bladder, pelvic floor and abdomen.
Figure 15:
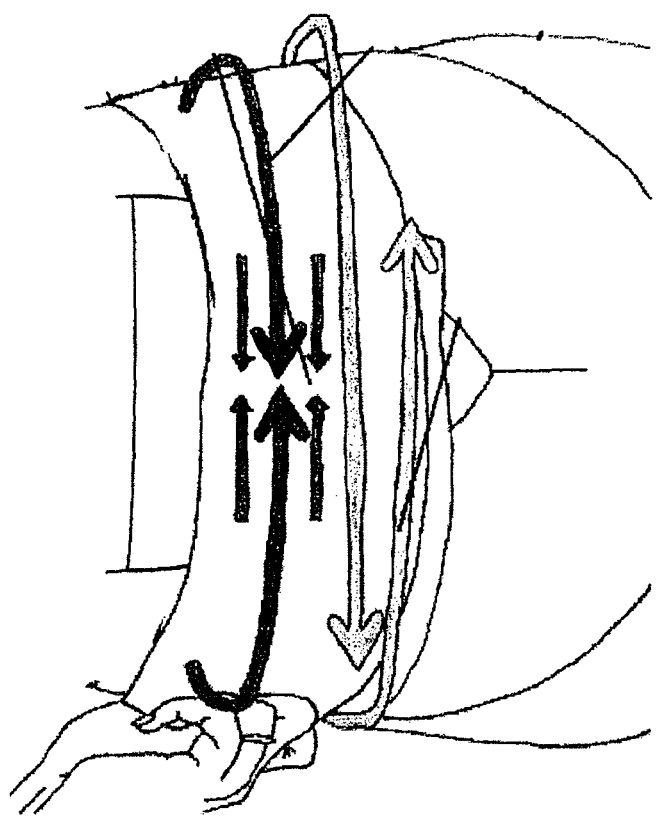
FIG. 15—is a rear view of the Diastasis Recti Splinting Garment. Small arrows demonstrate compression of the sacroiliac joints, created by the adjustable inner pelvic strap as it is pulled and wrapped around the pelvis. The larger arrows encircling the pelvis, represent the adjustable inner pelvic, bladder support and abdominal straps closing the lower portion of the cylinder providing a compression force on the abdomen, back and pelvis, balancing intra-abdominal pressure. This fosters stability of the system for optimal core activation and lower abdominal support and approximation.

The inner pelvic strap 62 is arranged so that the user can control the degree of compression based upon the tension that they generate as they pull and wrap the arms 64, 66 around the pelvis. The ability to adjust the position and tension of the arms 64, 66 of the inner pelvic strap as well as the attachment point allows for customization to best suit each individual user, thereby maximizing core and lumbopelvic stability, as well as providing pelvic floor/organ support and aid in balancing the intra-abdominal pressure, as discussed below and as shown in FIGS. 13, 14 and 15.

Figure 10:
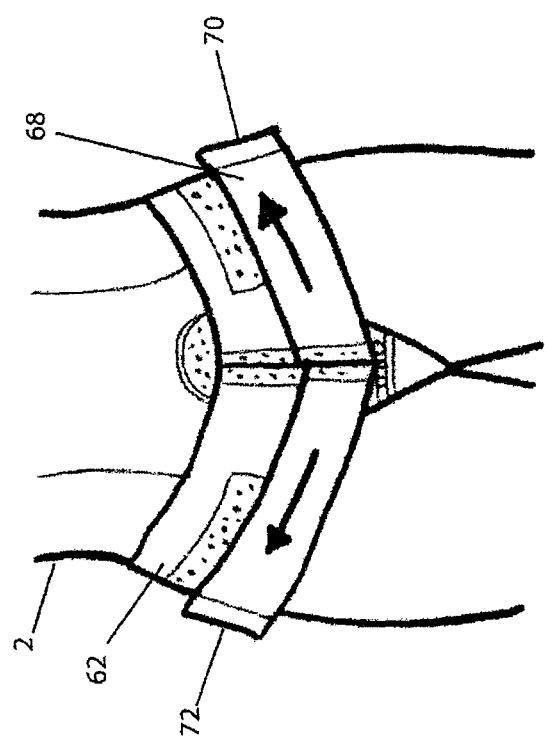
FIG. 10—is a front view of the detachable bladder support strap of the Diastasis Recti Splinting Garment originating from the front attachment of the inner pelvic strap. Arrows demonstrate the direction of pull by the user on the arms of the strap while wrapping around the pelvis.
Figure 11:
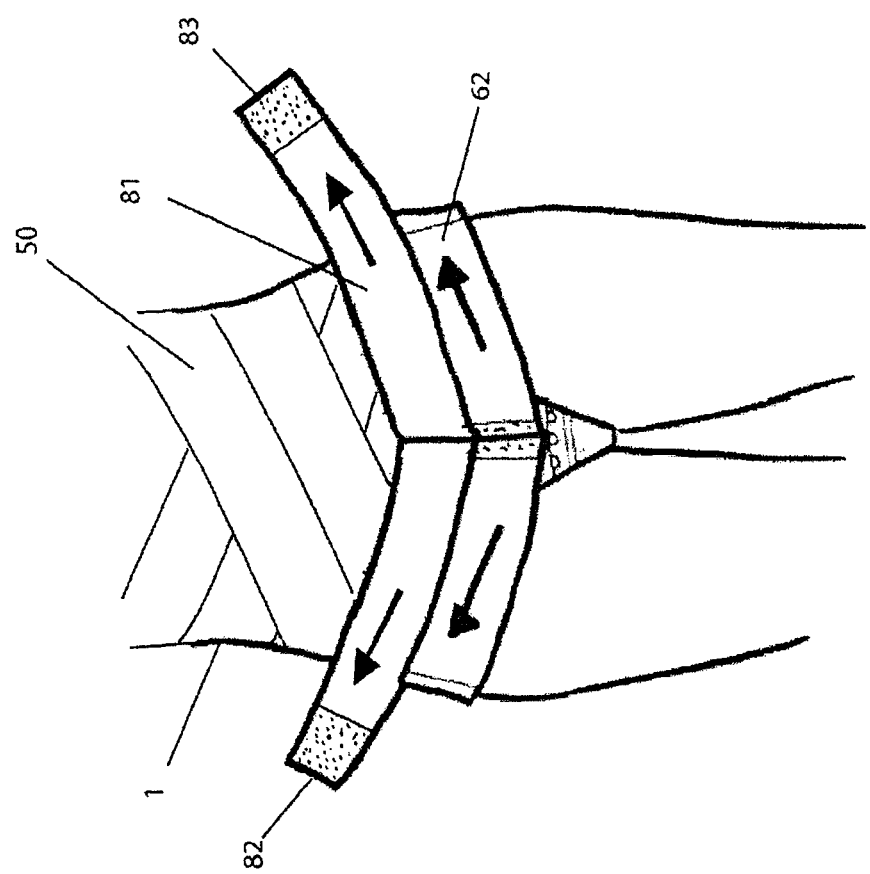
FIG. 11 is a front view of the detachable abdominal strap of the Diastasis Recti Splinting Garment in use originating from the front attachment of the inner pelvic strap. Arrows show the direction of pull by the user on the right and left arms of the strap while wrapping around the abdomen and pelvis towards the back.
Figure 12:
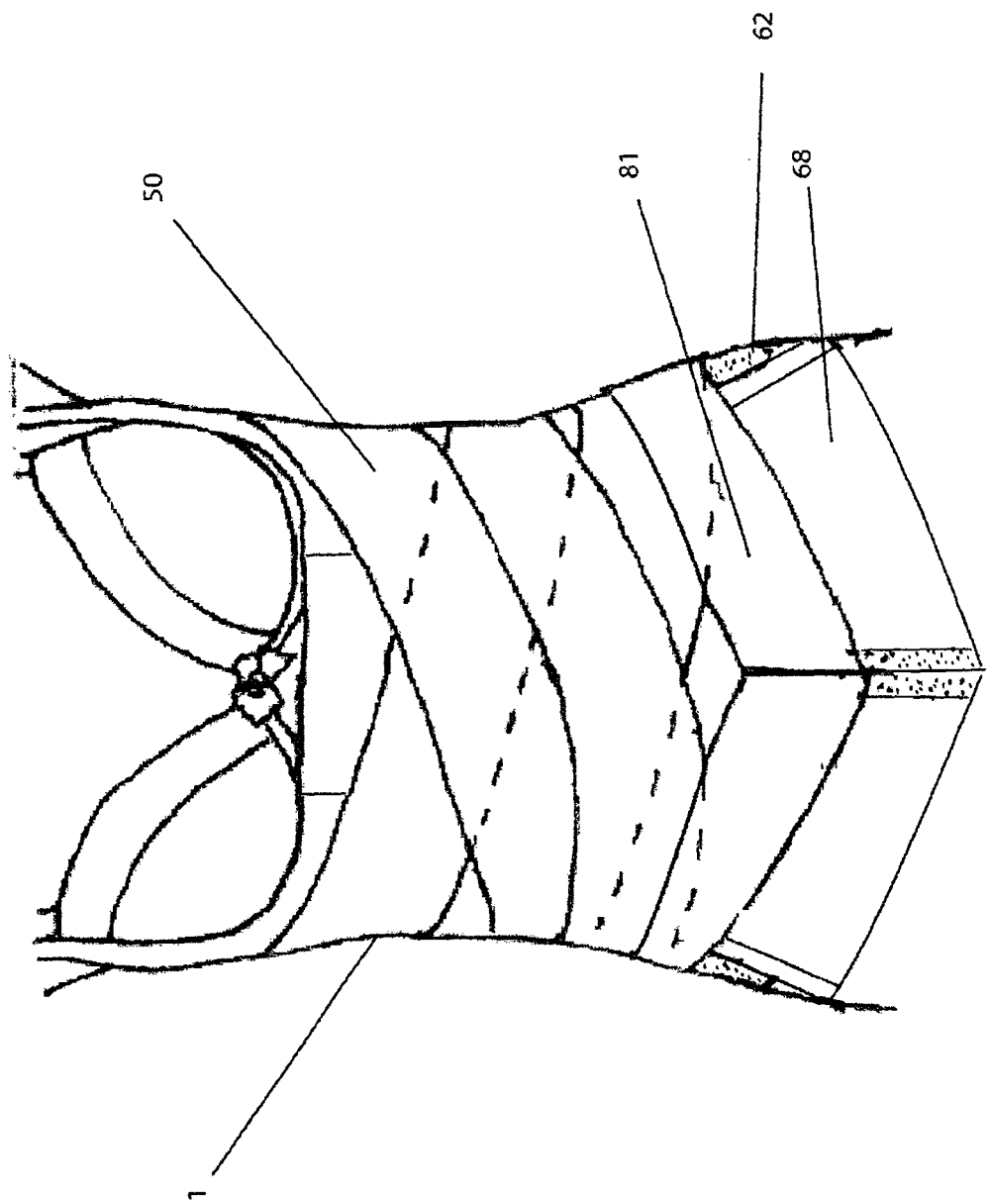
FIG. 12—is a front view of the abdominal strap in use, overlapping the right and left sets of torso straps.

As discussed herein, in some embodiments, the pelvic strap 60 is a dual strap and in addition to the inner pelvic strap also includes a bladder support strap 68 which is engaged by pulling both arms 70 and 72 upwardly at an oblique angle from the attachment point on the midline of the inner pelvic strap as shown in FIG. 10. The arms 70, 72 are pulled obliquely upward around the pelvis to the right and left respectively and are attached onto straps 64 and 66 respectively, as shown in FIG. 10. The bladder support strap 68 acts as a sling for the bladder and provides support for the generally weakened postpartum pelvic floor by providing support from below as well as aid in controlling intra-abdominal pressure from below. This can be visualized by review of FIGS. 13 and 14.

As discussed above, in other embodiments, there is provided a detachable abdominal strap 81 which can be attached directly and solely on the midline of the inner pelvic strap above the bladder support strap or alternately it can be placed in an overlapping manner on the bladder support strap and the inner pelvic strap. The right 82 and left 83 arms of the detachable abdominal strap are pulled upwardly and laterally on an oblique line from the attachment point around the pelvis to the right and left respectively. Based upon the user's needs the straps may attach to the rear connection panel and/or ends of torso straps and/or ends of inner pelvic straps individually or in an overlapping manner with said straps.

Depending on the body shape and/or body type of the user, the user may elect to also engage a wide torso strap 80. In some embodiments, the wide torso strap 80 is wider than the adjustable torso straps 51, 52, 53, 54. Exact placement and tension is determined by the individual user and is dependent on where support is needed. The attachable torso strap is wrapped around the body of the user on a diagonal angle, as discussed herein.

In use, the user can engage in usual activities or can engage in an exercise program, as discussed herein. In some embodiments, the body suit is made of a stretch compression fabric with a moisture management anti-microbial finish.

Specifically, with exercise and activity the body suit 2 design creates a garment 1 that prevents movement and slippage of the garment 1 during activity. This allows women to exercise and participate in activities of daily living comfortably. This is possible because of the compression and support provided by the garment.

Specifically, anatomically, the front central panel 30 mimics the placement of the rectus abdominis muscle, as well as the associated fascial sheathes of the rectus and the other abdominal musculature (transversus abdominal, internal oblique, external oblique). Functionally, the front central panel mimics one of the primary functions of the abdominal muscles and their associated sheathes, that of compression.

Furthermore, the front central panel 30 combines with the torso straps 50 to approximate the right and left side of the abdominal wall. The torso straps 50 are wrapped on the diagonal, this mimics the direction of the fibers of the external oblique muscles, approximating the right and left sides and creating a compression force as they cross midline, as can be seen in FIGS. 5, 6, 7, 8, 13, 16A and 16B.

Specifically, the crossing over of the torso straps 50 at midline is essential for the approximation and healing of the connective tissue. As the torso straps 50 are adjustable, the individual user is able to control the amount of compression based upon the tension created with the pull, as well as determine the exact oblique angle that is of greatest comfort and support to them.

The external oblique muscles have more than one action but contracting together results in compression of the abdomen, which is important in balancing intra-abdominal pressure and supporting the contents of the abdomen i.e., the organs (viscera). The other abdominal muscles including the internal obliques, the transversus abdominis as well as the rectus abdominis, also create compression of the abdomen when both the right and left sides contract together. This compression force produced by the straps, mimics the role of the abdominal muscles when they activate together.

The tensile force that is generated by the four adjustable torso straps 51, 52, 53, 54 and their attachment to the stretchable horizontal straps 46 of the upper portion 42 of the central back panel 40 as they are pulled and wrapped around the torso contributes to compression. This mimics the action of the abdominals and their associated fascial sheathes as well as the deep back muscles (i.e. multifidi), contributing to core stability, shown in FIGS. 13,14A, 14B, 16 A and 16B.

Furthermore, the upper portion 42 of the back central panel 40 allows for stability for the point of origin of the adjustable torso straps 51, 52, 53, 54 with the additional capability of creating an increase in tensile force (tension) for compression to support the abdominal contents as well as approximate the two sides of the abdominal wall. This occurs as the adjustable torso straps 51, 52, 53, 54 are stretched under load, when they are pulled forward and wrapped obliquely downwards around the torso to attach to the lower portion 44 of the back central panel 40 as well as the pelvic straps 60. Both the upper portion 42 and the lower portion 44 of the back central panel 40 mimic the location of the anatomical attachment points of some of the core musculature including the abdominal and back muscles. The lower portion 44 of the back central panel 40 has been designed and constructed to lend stability which is consistent with the role of the thoracolumbar fascia.

The inner pelvic strap 62 provides pelvic and core stability. It provides mild compression across the sacroiliac joints, as well as support to the low back and abdomen. The inner pelvic strap 62 mimics the action of the deep abdominal muscle, the transversus abdominis, which provides compression to the lower abdomen, supporting the organs and aids in balancing intra-abdominal pressure. The inner pelvic strap 62 also mimics the action of the ligaments of the sacroiliac joints and the posterior pelvic floor muscles, creating a compression force across the sacroiliac joints improving the stability of the pelvis. This compression also improves the stability of the lower (lumbar) spine, mimicking the stabilization function of the multifidi (deep back) muscles as shown in FIGS. 14A, 14B and 15.

In those embodiments wherein the bladder support strap 68 is engaged, the bladder support strap 68 acts as a sling for the bladder and provides support for the generally weakened postpartum pelvic floor by providing support from below, as shown in FIGS. 14A and 14B.

In these embodiments, the bladder support strap 68 and the inner pelvic strap 62 assist in balancing intra-abdominal pressure adjusting for any possible downward pressure gradient which may have developed from above secondary to the oblique downward wrap and attachment of the four adjustable torso straps 51, 52, 53, 54 as shown in FIG. 13.

As will be appreciated by one of skill in the art, the torso straps and pelvic strap(s) act synergistically to balance the intra-abdominal pressure. If you just have the torso straps, it will create a downward pressure gradient, possibly leading to incontinence or prolapse. If you just have the pelvic strap(s), you will create an upward pressure gradient that can cause bulging of the abdominal wall as well as affect the stability of the ribcage and function of the diaphragm. The torso straps are necessary to approximate and stabilize the two sides of the abdominal wall, to prevent abdominal bulging and any subsequent increase in the abdominal separation. Thus, the torso straps are necessary to balance the effect of the pelvic strap(s), and vice-versa, and both are needed to balance the intra-abdominal pressure which can be seen in FIG. 13.

The approximation of the abdominal wall and stabilization of the ribcage, trunk and spine achieved by the torso straps and the stabilization of the pelvis, sacroiliac joints and back with the pelvic straps, facilitates tissue healing but also allows for a stable base of support for the muscles to work properly. Without the pelvic strap(s), you do not have stabilization from below and without the torso straps you do not have approximation of the two sides of the abdominal wall and stabilization of the ribcage and cylinder from above, therefore no stable base of support as shown in FIGS. 15 and 16A.

As discussed herein, the four torso straps 51, 52, 53, 54 also function to re-establish an intact cylinder by approximating the right and left sides of the abdominal musculature that separates in the presence of a diastasis recti. The adjustable torso straps 51, 52, 53, 54 create abdominal compression, which together with the approximation allows for tissue healing at the area of separation (linea alba). Furthermore, the double layered design and fabric selection for the lower portion 44 of the back central panel 40 provides stability, thereby allowing for a base of support for the attachment of the adjustable torso straps 51, 52, 53, 54. The design and fabric selection also lends itself to compression, a necessary role to aid in closing the cylinder of the core, for stability and balanced intra-abdominal pressure, as discussed herein and as shown in FIGS. 13,15 and 16 A

The attachment region 32 provides a stable base of support for the pelvic strap 60, especially in those embodiments wherein the pelvic strap comprises the inner pelvic strap and the bladder support strap but also plays a dynamic role with increased tension being created with the compression fabric as the straps wrap and attach, closing the cylinder. This is consistent with the dynamic role of the thoracolumbar fascia with activation of the muscles.

Thus, the Diastasis Recti Splinting Garment 1 approximates the two sides of the abdominal wall, providing support to the linea alba to allow for tissue healing. Adjustable angled straps encircling the torso and pelvis restore the integrity of the core through this approximation, providing stability to the spine and pelvis. Restoring the integrity of the core lends itself to optimal activation of the deep core stabilizers, including the abdominal muscles as well as the musculature of the pelvic floor, back, and diaphragm. This in turn aids in dynamic stability of the ribcage, spine and pelvis.

As discussed herein, if necessary, the user can provide additional support to their abdominal wall and balance the intra-abdominal pressure gradient from below by engaging the attachable abdominal strap. Specifically, after the pelvic strap has been engaged, first and second arms of the abdominal strap are grasped and pulled on an upward oblique angle. Based upon the user's needs, the arms may attach to the rear connection panel, or to ends of torso straps or ends of inner pelvic straps individually or in an overlapping manner with the respective straps. Based upon the user's needs, the point of origin of the abdominal strap can be directly and solely on the front attachment of the inner pelvic strap above the bladder support strap or it can be placed in an overlapping manner with the bladder support strap with a shared point of origin from the front attachment of both of the straps (inner pelvic and bladder support).

Similarly, in some embodiments, there is provided a non-attached or attachable wide torso strap. In these embodiments, the user grasps one end of the attachable wide torso strap, and connects it to the back panel or the inner pelvic strap or back of the torso straps depending upon individual needs and wraps the attachable wide torso strap around the torso in an oblique manner, connecting the free end onto the body of the strap at an appropriate location. Utilization of this strap is determined by the user's needs According to one aspect of the invention, there is provided a Diastasis Recti splinting garment comprising:
  a body suit comprising:
    a front panel arranged to apply compression to the abdominal wall of a user;
    a back panel having an upper portion, and a lower portion, the lower portion having a rear connection panel; and
    at least two torso straps, said at least two torso straps arranged to be pulled and wrapped around the torso of the user and connect to the rear connection panel on the lower portion of the back panel; and
  a pelvic strap.

In some embodiments, each torso strap is arranged to wrap around the torso of the user in an oblique downward crossover starting on a first side of the midline of the user so that each respective adjustable torso strap crosses the midline of the user and connects to the rear connection panel on a second side of the midline of the user. The torso straps are attached simultaneously or sequentially.

In some embodiments, there are four torso straps, arranged such that a respective two adjustable torso straps are attached to each side of the body suit.

In some embodiments, the garment includes adjustable shoulder straps.

In some embodiments, the garment includes a groin panel which is arranged to be opened by the user without removal of the garment.

In some embodiments, the pelvic strap is a dual strap.

In some embodiments, the dual pelvic strap comprises an inner pelvic strap that is arranged to be pulled and wrapped around the pelvis of the user on an upward oblique angle and a bladder support strap arranged to be pulled and wrapped around the user on an upward oblique angle.

In some embodiments, an attachable wide torso strap is provided with the garment.

In some embodiments, the wide torso strap is arranged to be pulled and wrapped around the body of the user.

In some embodiments, there is provided an attachable abdominal strap. In these embodiments, based upon the user's needs the straps may attach to the rear connection panel, or to ends of torso straps or ends of inner pelvic straps individually or in an overlapping manner with said straps. Based upon the user's needs, the point of origin of the abdominal strap can be directly and solely on the front attachment of the inner pelvic strap above the bladder support strap or it can be placed in an overlapping manner with the bladder support strap with a shared point of origin from the front attachment of both of the straps (inner pelvic and bladder support).

According to another aspect of the invention, there is provided a method of supporting the abdomen, low back, ribcage, sacroiliac joints and pelvic floor of an individual suffering from diastasis recti, said individual having a body, a torso, a ribcage, a lower back, sacroiliac joints, an abdomen, a midline, abdominal musculature, a pelvis and a pelvic floor, said method comprising:
  providing a Diastasis Recti splinting garment comprising:
    a body suit comprising:
      a front panel arranged to apply compression to the abdominal wall of the individual;
      a back panel having an upper portion, and a lower portion, the lower portion having a rear connection panel; and
      at least two torso straps, said at least two torso straps arranged to be pulled and wrapped around the torso of the individual and connect to the rear connection panel on the lower portion of the back panel; and
    a pelvic strap;
  the user:
  (i) entering the body suit and positioning the body suit on the body of the user such that the front panel of the garment is placed on the abdominal musculature of the user, thereby providing compression to the abdominal musculature of the individual;
  (ii) grasping one of the at least two torso straps at a free end thereof and pulling and wrapping said one of the at least two torso straps around the torso of the individual at a downward oblique angle, crossing the free end over the midline of the individual and attaching the free end to the rear connection panel, thereby approximating right and left sides of the abdominal musculature; right and left straps are pulled across the midline simultaneously or sequentially to approximate the 2 sides of the abdominal wall;
  (iii) repeating step (ii) for each torso strap; and
  (iv) grasping the first and second arms of the pelvic strap and pulling and wrapping at an upward oblique angle and connecting the ends to the rear attachment panel, thereby providing compression across the sacroiliac joints of the user and supporting the lower back and the abdomen of the individual.

In some embodiments, the pelvic strap comprises an inner pelvic strap that is arranged to be pulled and wrapped around the pelvis of the individual at a upward oblique angle; and a bladder support strap arranged to be wrapped around the individual on an upward oblique angle.

In these embodiments, the method may further comprise step (v):
  (v) grasping first and second arms of the bladder support strap pulling both arms upwardly on an oblique angle, thereby providing support for the pelvic floor.

As discussed herein, if necessary, the user can provide additional support to their abdominal wall and balance the intra-abdominal pressure gradient from below by engaging the attachable abdominal strap Specifically, after the pelvic strap(s) has/have been engaged, first and second arms of the abdominal strap are grasped and pulled on an upward oblique angle. Based upon the user's needs, the arms may attach to the rear connection panel, or to ends of torso straps or ends of inner pelvic straps individually or in an overlapping manner with the respective straps. Based upon the user's needs, the point of origin of the abdominal strap can be directly and solely on the front attachment of the inner pelvic strap above the bladder support strap or it can be placed in an overlapping manner with the bladder support strap with a shared point of origin from the front attachment of both of the straps (inner pelvic and bladder support).

Similarly, in some embodiments, there is provided a non-attached or attachable wide torso strap. In these embodiments, the user grasps one end of the non-attached wide torso strap, and connects it to the back panel or the inner pelvic strap or back of the torso straps depending upon individual needs and wraps the attachable wide torso strap around the torso in an oblique manner, connecting the free end onto the body at an appropriate location. Utilization of this strap is determined by the user's needs In other embodiments, the user puts on the garment by
  (i) entering the body suit and positioning the body suit on the body of the user such that the front panel of the garment is placed on the abdominal wall of the user, thereby providing compression to the abdominal wall of the user;
  (ii) grasping a first end of the pelvic strap and pulling and wrapping the first end of the pelvic strap around the pelvis of the user on an upward oblique angle and connecting the first end to the rear attachment panel, thereby providing compression across the respective sacroiliac joint of the user and supporting the lower back and the abdomen of the user;
  (iii) grasping a second end of the pelvic strap and pulling and wrapping the second end of the inner pelvic strap around the pelvis of the user on an upward oblique angle and connecting the second end to the rear attachment panel, thereby providing compression across the sacroiliac joints of the user and supporting the lower back and the abdomen of the user;
  (iv) grasping one of the at least two torso straps at a free end thereof and pulling and wrapping said one of the at least two torso straps around the torso of the user on a downward oblique angle, crossing the free end over the midline of the user and continuing the wrap around the torso and pelvis to attach the free end to the rear connection panel on the opposite side; and (v) repeating step (iv) for each torso strap; the action of iv and v thereby stabilizing the ribcage, trunk, abdomen and back, and approximating the right and left sides of the abdominal musculature.

In some embodiments, the pelvic strap comprises an inner pelvic strap that is arranged to be pulled and wrapped around the pelvis of the individual at a upward oblique angle; and a bladder support strap arranged to be wrapped around the individual on an upward oblique angle.

In these embodiments, the method includes, following step (iii), step (iiia):

(iiia) grasping the first and second arms of the bladder support strap which attach at the center front of the inner pelvic strap, and pulling both arms upward on an oblique angle and connecting them to the inner pelvic strap, thereby providing support for the bladder, pelvic floor and abdomen as well as balancing the intra-abdominal pressure gradient from below.

In some embodiments, the method further includes an additional step, comprising grasping first and second arms of the abdominal strap and pulling both arms on an upward oblique angle, thereby providing support to the abdominal wall and balancing the intra-abdominal pressure gradient from below.

Based upon the user's needs, the point of origin of the abdominal strap can be directly and solely on the front attachment of the inner pelvic strap above the bladder support strap or it can be placed in an overlapping manner with the bladder support strap with a shared point of origin from the front attachment of both of the straps (inner pelvic and bladder support).

In yet other embodiments, the method includes an additional step, comprising grasping one end of the attachable wide torso strap, the user connects it to the back panel or the inner pelvic strap or back of the torso straps depending upon individual needs and wraps the strap around the torso in an oblique manner connecting the free end onto the body of the strap. Utilization of this strap is determined by the user's needs, as discussed herein.

In some embodiments a free end of one of the torso straps may also attach to the inner pelvic strap, depending upon the needs of the user.

Based upon the user's needs the straps may attach to the rear connection panel, ends of torso straps and ends of inner pelvic straps individually or in an overlapping manner with said straps.

In some embodiments, as discussed herein, there is provided an attachable abdominal strap so that the user can provide additional support to their abdominal wall and balance the intra-abdominal pressure gradient from below by engaging the attachable abdominal strap.

In some embodiments, each torso strap is pulled and wrapped around the torso of the individual so as to cross over a previously engaged torso strap.

In some embodiments, there are four torso straps, arranged such that a respective two adjustable torso straps are attached to each side of the body suit.

In some embodiments, the garment includes adjustable shoulder straps and the user adjusts the shoulder straps after entering the body suit.

In some embodiments, the garment includes a groin panel which is closed by the user after entering the body suit.

In some embodiments, an attachable wide torso strap is provided with the garment which is pulled and wrapped around the body of the individual, thereby supplying additional compression in the abdomen and supporting the approximation of the right and left sides of the abdominal musculature.

The invention will now be further explained and elucidated by way of examples; however, the invention is not necessarily limited to the examples.

To trial the garment, a study was conducted on 8 women with each having a diastasis recti. They were asked to perform a series of 7 activities without the garment and then repeat these activities with the garment in place.

Figure 18:
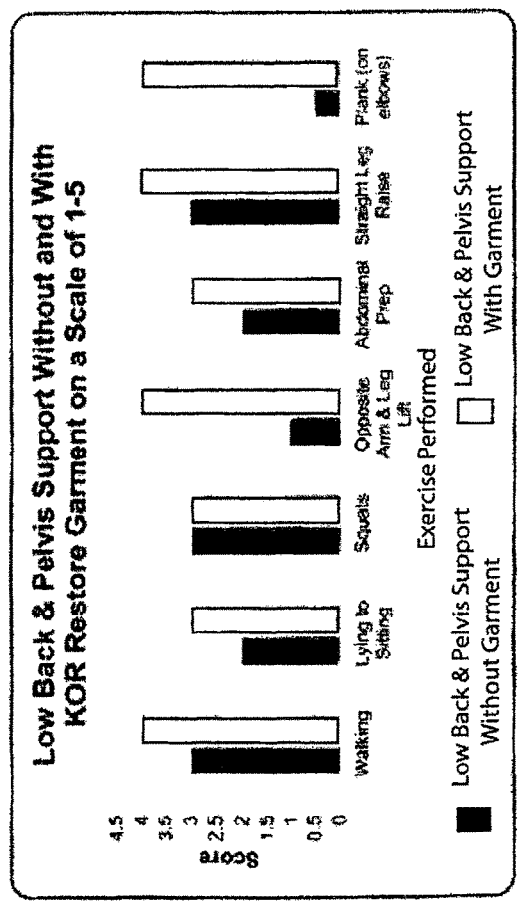
FIG. 18 is a graph representing results obtained with testing of the Diastasis Recti Splinting Garment in regards to low back and pelvis support.
Figure 19:
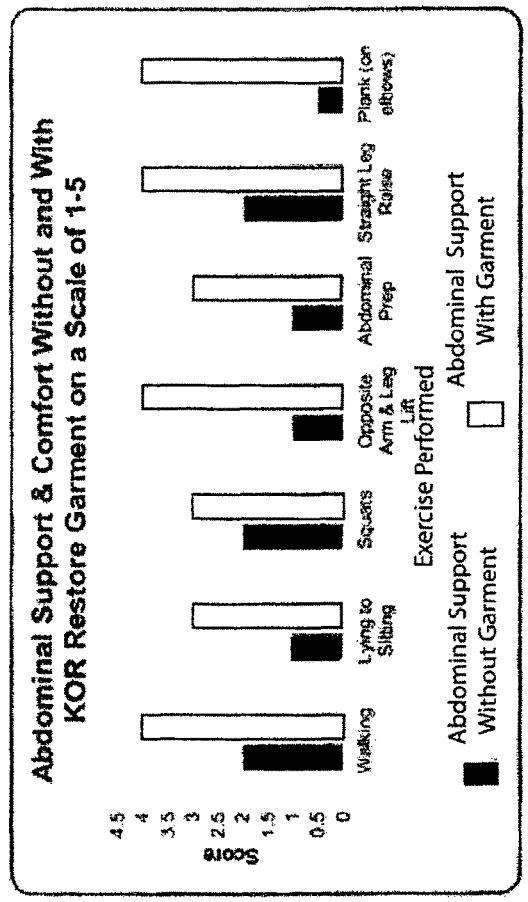
FIG. 19—is a graph representing results obtained with testing of the Diastasis Recti Splinting Garment in regards to abdominal support and comfort.

The following activities were performed:
1. Walking on a treadmill
2. Position change: moving from a lying to a sitting position
3. Squat
4. Opposite arm and leg lift
5. Abdominal prep (partial abdominal curl)
6. Straight leg raise
7. Plank The results indicated that the subjects noted significant improvements in abdominal support and comfort with the garment in place across all exercises and functional activities performed, with improvements noted in low back and pelvis support across 6 of the 7 activities, as shown in FIGS. 18 and 19.

The subjects were also asked to comment on the garment. Feedback from the initial trial was utilized to adjust the garment with 3 women returning to retry the garment, once the changes were made.

Specifically, it was reported that the garment made the pelvis of the users feel very secure, provided great support to their abdomen, was comfortable during exercise and was convenient for breastfeeding.

Furthermore, it was noted that the garment material was very breathable and comfortable, provided great support to low back, pelvis and abdomen and helped maintain good posture during exercise One user said "I honestly did not want to take the garment off! It gave me the full body support that I need while standing, sitting and doing basic exercises. It helped me feel like I could actually hold my body up with proper posture, which has been extremely difficult since my two C-sections."

Another user said "when I wore the garment to exercise, I felt held in and supported. I needed the garment for workouts to help heal my diastasis recti and to prevent it from getting worse."

As discussed herein, in some embodiments, the garment is to be used in conjunction with a core/pelvic floor program with the focus on neuromuscular re-training to maximize recovery potential from a diastasis recti. The program emphasizes the importance of correct posture or body position, so the muscles of the core are optimally recruited. Although the focus is core, the program is a whole-body approach looking at the head, neck, shoulder girdle, torso and all the way to the feet.

The exercise program includes stretches for the lower extremities, low back, shoulder girdle and chest. Self-release techniques utilizing a ball and gentle pressure are also included to emphasize opening the chest and releasing the diaphragm and hip flexors which all impact the tension on the linea alba. Diaphragmatic breathing exercises are incorporated to improve core muscle recruitment and control of intra-abdominal pressure. Cardiovascular exercise is also included to improve heart health and general mobility. The type of cardio activity is to the individual's discretion depending on what is available to them (walking, biking, stepping, etc.).

The core strengthening exercises start with activation of the pelvic floor muscles first in isolation, then working on endurance and speed. This is progressed to connecting the pelvic floor with the rest of the core musculature and maintaining this active connection with movement. The program is working the body globally, incorporating trunk and scapular stability exercises as well as upper and lower body strengthening with functional goals (i.e., squats, lunges, arm raises with resistance) with the key focus of maintaining the inner core activation to allow for spinal stability and balanced intra-abdominal pressure. The exercises in the program are progressed every 2 weeks for a total of 10 weeks.

The scope of the claims should not be limited by the preferred embodiments set forth in the examples but should be given the broadest interpretation consistent with the description as a whole.

REFERENCES

Atlas: Musculus transversus abdominis. (2018). Retrieved from Ken Hub Website: https://www.kenhub.com
Carrière, B., & Feldt, C. (2006). The Pelvic Floor. New York, N.Y.: Thieme.
Coldron, Y., Stokes, M. J., & Cook, K. (2007). Postpartum characteristics of rectus abdominis on ultrasound imaging. Manual Therapy.
Gilleard, W. L., & Brown, J. M. (1996, July). Structure and function of the abdominal muscles in primigravida during pregnancy and the immediate post-birth period. Physical Therapy, 76(7).
Lee, D. (2018, February). Article: Diastasis Rectus Abdominus. Retrieved from Diane Lee & Associates Website: http://dianelee.ca
Liaw, L., Hsu, M., Liao, C., Liu, M., & HSU, A. (2011, June). The relationshipos between inter-recti distance measured by ultrasound imaging and abdominal muslce function in postpartum women: a 6-month follow up study. Ortho Sports Phys Ther, 41(6), 435-43.
Netter, F. (2017). Atlas of Human Anatomy. Philadelphia: Elsevier.
Paturel, A. (2017, January). https://www.babycenter.com/0_diastasis-recti_10419293.bc. Retrieved from Baby Center Website: https://www.babycenter.com/0_d iastasis-recti_10419293.bc
Rectus Abdominius Muscle: Function Of Rectus Abdominis Muscle. (2014). Retrieved from Human Anatomy Diagram Website: https://anatomychartee.co
Singh, A. P. (2016, September 1). Muscles of abdominal wall. Retrieved from Med Care Tips Website: http://medcaretips.com
Spitznagle, T., Leong, F., & Van Dillen, L. (2007, March). Prevalence of diastasis recti abdominis in a urogynecological patient population. Int Urogynecol J Pelvic Floor Dysfunct., 18, 321-328.

The invention claimed is:

1. A Diastasis Recti splinting garment comprising:
   a body suit comprising:
      a front panel arranged to apply compression to an abdominal wall of a user;
      a back panel having an upper portion, and a lower portion, the lower portion having a rear connection panel; and
      at least two adjustable torso straps, said at least two adjustable torso straps arranged to be pulled and wrapped around a torso of the user and connect to the rear connection panel on the lower portion of the back panel; and
   an attachable pelvic strap arranged to be pulled and wrapped around a pelvis of the user on an upward oblique angle and connect to the rear connection panel on the lower portion of the back panel.

2. The garment according to claim 1 wherein each adjustable torso strap is arranged to be pulled and wrapped around the torso of the user on an oblique downward crossover starting on a first side of a midline of the user so that each respective adjustable torso strap crosses the midline of the user and connects to the rear connection panel on a second side of the midline of the user.

3. The garment according to claim 1 wherein there are four adjustable torso straps, arranged such that a respective two adjustable torso straps are attached to each side of the body suit.

4. The garment according to claim 1 wherein the pelvic strap is a dual strap.

5. The garment according to claim 4 wherein the dual strap comprises an inner pelvic strap that is arranged to be pulled and wrapped around the pelvis of the user on an upward oblique angle and a bladder support strap arranged to be wrapped around the user on an upward oblique angle.

6. The garment according to claim 1 wherein an attachable wide torso strap is provided with the garment.

7. The garment according to claim 6 wherein the wide torso strap is arranged to be pulled and wrapped around the torso of the user.

8. The garment according to claim 1 wherein an attachable abdominal strap arranged to be pulled and wrapped around an abdomen of the user is provided.

9. A method of supporting the abdomen of a user suffering from diastasis recti, said user-having a body, a torso, a ribcage, a lower back, sacroiliac joints, an abdomen, a midline, an abdominal wall, abdominal musculature, a pelvis and a pelvic floor, said method comprising:
   providing a Diastasis Recti splinting garment comprising:
      a body suit comprising:
         a front panel arranged to apply compression to the abdominal wall of the user;
         a back panel having an upper portion, and a lower portion, the lower portion having a rear connection panel; and
         at least two adjustable torso straps, said at least two adjustable torso straps arranged to be pulled and wrapped around the torso of the user and connect to the rear connection panel on the lower portion of the back panel; and
      a pelvic strap that is arranged to be pulled and wrapped around the pelvis of the user on an upward oblique angle;
   the user:
      (i) entering the body suit and positioning the body suit on the body of the user such that the front panel of the garment is placed on the abdominal musculature of the user, thereby providing compression to the abdominal musculature of the user;
      (ii) grasping one of the at least two adjustable torso straps at a free end thereof and pulling and wrapping said one of the at least two adjustable torso straps around the torso of the user on a downward oblique angle, crossing the free end over the midline of the user and attaching the free end to the rear connection panel, thereby approximating right and left sides of the abdominal musculature of the user;

(iii) repeating step (ii) for each adjustable torso strap;

(iv) grasping a first end of the pelvic strap and pulling and wrapping the first end of the pelvic strap around the pelvis of the user on an upward oblique angle and connecting the first end to the rear attachment panel, thereby providing compression across the respective sacroiliac joint of the user and supporting the lower back and the abdomen of the user; and (v) grasping a second end of the pelvic strap and pulling and wrapping the second end of the pelvic strap around the pelvis of the user on an upward oblique angle and connecting the second end to the rear attachment panel, thereby providing compression across the sacroiliac joints of the user and supporting the lower back and the abdomen of the user.

10. The method according to claim 9 wherein the pelvic strap comprises an inner pelvic strap and a bladder support strap arranged to be wrapped around the user in an upper oblique angle and wherein the method further comprises:
(vi) grasping first and second arms of the bladder support strap and pulling both arms upwardly on an oblique angle, thereby providing support for the pelvic floor.

11. The method according to claim 9 wherein each adjustable torso strap is pulled and wrapped around the torso of the user so as to cross over a previously engaged adjustable torso strap.

12. The method according to claim 9 wherein there are four adjustable torso straps, arranged such that a respective two adjustable torso straps are attached to each side of the body suit.

13. The method according to claim 9 wherein a wide torso strap is provided with the garment which is pulled and wrapped around the torso of the user, thereby supplying additional compression.

14. The method according to claim 9 wherein an attachable abdominal support strap is provided with the garment which is pulled and wrapped around the abdomen of the user, thereby supplying additional compression to the abdominal wall and aiding in balancing the downward intra-abdominal pressure gradient created from the adjustable torso straps above.

15. A method of supporting the abdomen of a user suffering from diastasis recti, said user having a body, a torso, a ribcage, a lower back, sacroiliac joints, an abdomen, a midline, an abdominal wall, abdominal musculature, a pelvis and a pelvic floor, said method comprising:
providing a Diastasis Recti splinting garment comprising:
a body suit comprising:
a front panel arranged to apply compression to the abdominal wall of the user;
a back panel having an upper portion, and a lower portion, the lower portion having a rear connection panel; and
at least two adjustable torso straps, said at least two adjustable torso straps arranged to be pulled and wrapped around the torso of the user and connect to the rear connection panel on the lower portion of the back panel; and
a pelvic strap that is arranged to be pulled and wrapped around the pelvis of the user on an upward oblique angle;
the user:

(i) entering the body suit and positioning the body suit on the body of the user such that the front panel of the garment is placed on the abdominal wall of the user, thereby providing compression to the abdominal wall of the user;

(ii) grasping a first end of the pelvic strap and pulling and wrapping the first end of the pelvic strap around the pelvis of the user on an upward oblique angle and connecting the first end to the rear attachment panel, thereby providing compression across the respective sacroiliac joint of the user and supporting the lower back and the abdomen of the user;

(iii) grasping a second end of the pelvic strap and pulling and wrapping the second end of the pelvic strap around the pelvis of the user on an upward oblique angle and connecting the second end to the rear attachment panel, thereby providing compression across the sacroiliac joints of the user and supporting the lower back and the abdomen of the user;

(iv) grasping one of the at least two adjustable torso straps at a free end thereof and pulling and wrapping said one of the at least two adjustable torso straps around the torso of the user on a downward oblique angle, crossing the free end over the midline of the user and continuing the wrap around the torso and pelvis to attach the free end to the rear connection panel on an opposite side; and (v) repeating step (iv) for each adjustable torso strap; the action of steps (iv) and (v) stabilizing the ribcage, the torso, the abdomen and the lower back, thereby approximating the right and left sides of the abdominal musculature.

16. The method according to claim 15 wherein the pelvic strap comprises an inner pelvic strap and a bladder support strap arranged to be wrapped around the user on an upper oblique angle and wherein the method further comprises: after step (iii), step (iiia): grasping first and second arms of the bladder support strap and pulling both arms upwardly on an oblique angle, thereby providing support for the pelvic floor.

17. The method according to claim 15 wherein each adjustable torso strap is pulled and wrapped around the torso of the user so as to cross over a previously engaged adjustable torso strap.

18. The method according to claim 15 wherein there are four adjustable torso straps, arranged such that a respective two adjustable torso straps are attached to each side of the body suit.

19. The method according to claim 15 wherein a wide torso strap is provided with the garment which is pulled and wrapped around the torso of the user, thereby supplying additional compression.

20. The method according to claim 15 wherein an attachable abdominal support strap is provided with the garment which is pulled and wrapped around the abdomen of the user on an upward oblique angle, thereby supplying additional compression to the abdominal wall and aiding in balancing the downward intra-abdominal pressure gradient created from the adjustable torso straps above.

* * * * *